(12) United States Patent
Gray

(10) Patent No.: US 12,296,026 B2
(45) Date of Patent: May 13, 2025

(54) TRANSCRIPTION REGULATORY ELEMENTS AND USES THEREOF

(71) Applicant: Audentes Therapeutics, Inc., San Francisco, CA (US)

(72) Inventor: John T. Gray, San Francisco, CA (US)

(73) Assignee: Astellas Gene Therapies, Inc., South San Francisco, CA (US)

(*) Notice: Subject to any disclaimer, the term of this patent is extended or adjusted under 35 U.S.C. 154(b) by 1109 days.

(21) Appl. No.: 16/966,521

(22) PCT Filed: Feb. 5, 2019

(86) PCT No.: PCT/US2019/016692
§ 371 (c)(1),
(2) Date: Jul. 31, 2020

(87) PCT Pub. No.: WO2019/153009
PCT Pub. Date: Aug. 8, 2019

(65) Prior Publication Data
US 2021/0162073 A1    Jun. 3, 2021

Related U.S. Application Data

(60) Provisional application No. 62/626,561, filed on Feb. 5, 2018.

(51) Int. Cl.
*A61K 48/00* (2006.01)
*A61P 3/00* (2006.01)
*C12N 7/00* (2006.01)
*C12N 15/86* (2006.01)

(52) U.S. Cl.
CPC .......... *A61K 48/0058* (2013.01); *A61P 3/00* (2018.01); *C12N 7/00* (2013.01); *C12N 15/86* (2013.01); *C12N 2750/14143* (2013.01); *C12N 2830/008* (2013.01)

(58) Field of Classification Search
CPC ............... A61K 48/0058; C12N 15/86; C12N 2830/008
USPC ........................................................ 435/370
See application file for complete search history.

(56) References Cited

U.S. PATENT DOCUMENTS

| | | |
|---|---|---|
| 8,030,065 B2 | 10/2011 | Gray |
| 8,168,425 B2 | 5/2012 | Gray |
| 2007/0161031 A1 | 7/2007 | Trinklein et al. |
| 2010/0120152 A1 | 5/2010 | Wooddell et al. |
| 2017/0218395 A1 | 8/2017 | Byrne et al. |
| 2017/0275649 A1 | 9/2017 | Vandendriessche et al. |

FOREIGN PATENT DOCUMENTS

| | | |
|---|---|---|
| EP | 1804839 A2 | 7/2007 |
| EP | 2438931 A1 | 4/2012 |
| WO | WO-02/095006 A2 | 11/2002 |
| WO | WO-2015/110449 A1 | 7/2015 |
| WO | WO-2015/196179 A1 | 12/2015 |

OTHER PUBLICATIONS

Gehrke (2003, Gene, 322:137-143).*
Doerfler et al., "Copackaged AAV9 Vectors Promote Simultaneous Immune Tolerance and Phenotypic Correction of Pompe Disease," Hum Gene Ther. 27(1):43-59 (2016).
Chu et al., "Induction of Immune Tolerance to a Therapeutic Protein by Intrathymic Gene Delivery," Mol. Ther. 18(12):2146-54 (2010).
Gao et al., "A Novel Site, Mt, in the Human Desmin Enhancer is Necessary for Maximal Expression in Skeletal Muscle," J Biol Chem. 273(11):6402-09 (1998) (9 pages).
International Search Report and Written Opinion for International Patent Application No. PCT/US2019/016692, mailed Jun. 18, 2019 (20 pages).
Kwissa et al., "Efficient vaccination by intradermal or intramuscular inoculation of plasmid DNA expressing hepatitis B surface antigen under desmin promoter/enhancer control," Vaccine. 18(22):2337-44 (2000).
Li et al., "High Level Desmin Expression Depends on a Muscle-specific Enhancer," J Biol Chem. 256(10):6562-70 (1991).
Pacak et al., "Tissue specific promoters improve specificity of AAV9 mediated transgene expression following intra-vascular gene delivery in meonatal mice," Genet Vaccine Ther. 6(13):doi: 10.1186/1479-0556-6-13 (2008) (5 pages).
Pacak, Christina A., Thesis: "Gene Delivery Strategies for The Treatment of Cardiac and Skeletal Muscle in Murine Models of Muscular Dystrophy," Doctor of Philosophy, University of Florida, 2006 (151 pages).

* cited by examiner

*Primary Examiner* — Valarie E Bertoglio
(74) *Attorney, Agent, or Firm* — Clark & Elbing LLP

(57) ABSTRACT

The invention provides regulatory elements, as well as vectors containing the same that may be used to stimulate transcription of a gene of interest in certain tissue types. The transcription regulatory elements described herein may be operably linked to a transgene, such as acid alpha-glucosidase (GAA), so as to promote expression of the GAA transgene in a cell, such as a muscle cell, liver cell, or neuron. The transcription regulatory elements described herein may be operably linked to a therapeutic transgene and used for the treatment of various disorders, such as lysosomal storage diseases, and particularly Pompe disease.

11 Claims, 11 Drawing Sheets
Specification includes a Sequence Listing.

SEQUENCE LISTING

```
<160> NUMBER OF SEQ ID NOS: 14

<210> SEQ ID NO 1
<211> LENGTH: 193
<212> TYPE: DNA
<213> ORGANISM: Artificial Sequence
<220> FEATURE:
<223> OTHER INFORMATION: Synthetic Construct

<400> SEQUENCE: 1
cccctaaaat gggcaaacat tgcaagcagc aaacagcaaa cacacagccc tccctgcctg        60
ctgaccttgg agctggggca gaggtcagag acctctctgg gcccatgcca cctccaacat       120
ccactcgacc ccttggaatt tcggtggaga ggagcagagg ttgtcctggc gtggtttagg       180
tagtgtgaga ggg                                                         193

<210> SEQ ID NO 2
<211> LENGTH: 320
<212> TYPE: DNA
<213> ORGANISM: Artificial Sequence
<220> FEATURE:
<223> OTHER INFORMATION: Synthetic Construct

<400> SEQUENCE: 2
ggctcagagg cacacaggag tttctgggct caccctgccc ccttccaacc cctcagttcc        60
catcctccag cagctgtttg tgtgctgcct ctgaagtcca cactgaacaa acttcagcct       120
actcatgtcc ctaaaatggg caaacattgc aagcagcaaa cagcaaacac acagccctcc       180
ctgcctgctg accttggagc tggggcagag gtcagagacc tctctgggcc catgccacct       240
ccaacatcca ctcgacccct tggaatttcg gtggagagga gcagaggttg tcctggcgtg       300
gtttaggtag tgtgagaggg                                                  320

<210> SEQ ID NO 3
<211> LENGTH: 774
<212> TYPE: DNA
<213> ORGANISM: Artificial Sequence
<220> FEATURE:
<223> OTHER INFORMATION: Synthetic Construct

<400> SEQUENCE: 3
ctgcaggctc agaggcacac aggagtttct gggctcaccc tgcccccttc caacccctca        60
gttcccatcc tccagcagct gtttgtgtgc tgcctctgaa gtccacactg aacaaacttc       120
agcctactca tgtccctaaa atgggcaaac attgcaagca gcaaacagca aacacacagc       180
cctccctgcc tgctgacctt ggagctgggg cagaggtcag agacctctct gggcccatgc       240
cacctccaac atccactcga ccccttggaa tttcggtgga gaggagcaga ggttgtcctg       300
gcgtggttta ggtagtgtga gagggtccgg gttcaaaacc acttgctggg tggggagtcg       360
tcagtaagtg gctatgcccc gaccccgaag cctgtttccc catctgtaca atggaaatga       420
taaagacgcc catctgatag ggttttttgtg gcaaataaac atttggtttt tttgtttttgt       480 tttgttttgt tttttgagat ggaggtttgc tctgtcgccc aggctggagt gcagtgacac       540
aatctcatct caccacaacc ttcccctgcc tcagcctccc aagtagctgg gattacaagc       600
```

```
atgtgccacc acacctggct aatttctat ttttagtaga gacgggtttc tccatgttgg    660
tcagcctcag cctcccaagt aactgggatt acaggcctgt gccaccacac ccggctaatt    720
ttttctattt ttgacaggga cggggtttca ccatgttggt caggctggtc taga          774

<210> SEQ ID NO 4
<211> LENGTH: 50
<212> TYPE: DNA
<213> ORGANISM: Artificial Sequence
<220> FEATURE:
<223> OTHER INFORMATION: Synthetic Construct

<400> SEQUENCE: 4
cccctaaaat gggcaaacat tgcaagcagc aaacagcaaa cacacagccc                 50

<210> SEQ ID NO 5
<211> LENGTH: 342
<212> TYPE: DNA
<213> ORGANISM: Artificial Sequence
<220> FEATURE:
<223> OTHER INFORMATION: Synthetic Construct

<400> SEQUENCE: 5
taccccctgc ccccacagc tcctctcctg tgccttgttt cccagccatg cgttctcctc      60
tataaatacc cgctctggta tttggggttg gcagctgttg ctgccaggga gatggttggg    120
ttgacatgcg gctcctgaca aaacacaaac ccctggtgtg tgtgggcgtg ggtggtgtga    180
gtagggggat gaatcaggga gggggcgggg gacccagggg gcaggagcca cacaaagtct    240 gtgcggggt gggagcgcac atagcaattg gaaactgaaa gcttatcaga ccctttctgg    300
aaatcagccc actgtttata aacttgaggc cccaccctcg ag                       342

<210> SEQ ID NO 6
<211> LENGTH: 346
<212> TYPE: DNA
<213> ORGANISM: Artificial Sequence
<220> FEATURE:
<223> OTHER INFORMATION: Synthetic Construct

<400> SEQUENCE: 6
cgagataacc agggctgaaa gaggcccgcc tggggctgg agacatgctt gctgcctgcc      60
ctggcgaagg attggcaggc ttgcccgtca caggaccccc gctggctgac tcaggggcgc    120
aggcctcttg cgggggagct ggcctccccg ccccacggc cacgggccgc cctttcctgg    180
caggacagcg ggatcttgca gctgtcaggg gaggggaggc gggggctgat gtcaggaggg    240
atacaaatag tgccgacggc tggggccct gtctcccctc gccgcatcca ctctccggcc    300
ggccgcctgt ccgccgcctc ctccgtgcgc ccgccagcct cgcccg                   346

<210> SEQ ID NO 7
<211> LENGTH: 688
<212> TYPE: DNA
<213> ORGANISM: Artificial Sequence
<220> FEATURE:
<223> OTHER INFORMATION: Synthetic Construct

<400> SEQUENCE: 7
taccccctgc ccccacagc tcctctcctg tgccttgttt cccagccatg cgttctcctc      60
tataaatacc cgctctggta tttggggttg gcagctgttg ctgccaggga gatggttggg    120
ttgacatgcg gctcctgaca aaacacaaac ccctggtgtg tgtgggcgtg ggtggtgtga    180
```

| | |
|---|---|
| gtaggggat gaatcaggga gggggcgggg gacccagggg gcaggagcca cacaaagtct | 240 |
| gtgcggggt gggagcgcac atagcaattg gaaactgaaa gcttatcaga cccttctgg | 300 |
| aaatcagccc actgtttata aacttgaggc cccaccctcg agcgagataa ccagggctga | 360 |
| aagaggcccg cctgggggct ggagacatgc ttgctgcctg ccctggcgaa ggattggcag | 420 |
| gcttgcccgt cacaggaccc ccgctggctg actcaggggc gcaggcctct tgcggggag | 480 |
| ctggcctccc cgcccacg gccacgggcc gcccttcct ggcaggacag cgggatcttg | 540 |
| cagctgtcag gggaggggag gcgggggctg atgtcaggag ggatacaaat agtgccgacg | 600 |
| gctgggggcc ctgtctcccc tcgccgcatc cactctccgg ccggccgcct gtccgccgcc | 660 |
| tcctccgtgc gcccgccagc ctcgcccg | 688 |

<210> SEQ ID NO 8
<211> LENGTH: 375
<212> TYPE: DNA
<213> ORGANISM: Artificial Sequence
<220> FEATURE:
<223> OTHER INFORMATION: Synthetic Construct

<400> SEQUENCE: 8

| | |
|---|---|
| aaaatgcctt ctgagttgaa tatcaacact acaaaccgag tatctgcaga gggccctgcg | 60 |
| tatgagtgca agtgggtttt aggaccagga tgaggcgggg tgggggtgcc tacctgacga | 120 |
| ccgaccccga cccactggac aagcacccaa cccccattcc ccaaattgcg catcccctat | 180 |
| cagagagggg gaggggaaac aggatgcggc gaggcgcgtg cgcactgcca gcttcagcac | 240 |
| cgcggacagt gccttcgccc ccgcctggcg gcgcgcgcca ccgccgcctc agcactgaag | 300 |
| gcgcgctgac gtcactcgcc ggtccccgc aaactcccct tcccggccac cttggtcgcg | 360 |
| tccgcgccgc cgccg | 375 |

<210> SEQ ID NO 9
<211> LENGTH: 449
<212> TYPE: DNA
<213> ORGANISM: Artificial Sequence
<220> FEATURE:
<223> OTHER INFORMATION: Synthetic Construct

<400> SEQUENCE: 9

| | |
|---|---|
| cccctaaaat gggcaaacat tgcaagcagc aaacagcaaa cacacagccc tccctgcctg | 60 |
| ctgaccttgg agctggggca gaggtcagag acctctctgg gcccatgcca cctccaacat | 120 |
| ccactcgacc ccttggaatt tcggtggaga ggagcagagg ttgtcctggc gtggtttagg | 180 |
| tagtgtgaga ggggaatgac tccttttcggt aagtgcagtg gaagctgtac actgcccagg | 240 |
| caaagcgtcc gggcagcgta ggcggcgac tcagatccca gccagtgcac ttagcccctg | 300 |
| tttgctcctc cgataactgg ggtgaccttg gttaatattc accagcagcc tccccgttg | 360 |
| cccctctgga tccactgctt aaatacggac gaggacaggg ccctgtctcc tcagcttcag | 420 |
| gcaccaccac tgacctggga cagtgaatc | 449 |

<210> SEQ ID NO 10
<211> LENGTH: 881
<212> TYPE: DNA
<213> ORGANISM: Artificial Sequence
<220> FEATURE:
<223> OTHER INFORMATION: Synthetic Construct

<400> SEQUENCE: 10

```
cccctaaaat gggcaaacat tgcaagcagc aaacagcaaa cacacagccc tccctgcctg        60
ctgaccttgg agctggggca gaggtcagag acctctctgg gcccatgcca cctccaacat       120
ccactcgacc ccttggaatt tcggtggaga ggagcagagg ttgtcctggc gtggtttagg       180
tagtgtgaga gggtacccccc tgcccccac agctcctctc ctgtgccttg tttcccagcc      240
atgcgttctc ctctataaat acccgctctg gtatttgggg ttggcagctg ttgctgccag       300
ggagatggtt gggttgacat gcggctcctg acaaaacaca aaccccctggt gtgtgtgggc      360
gtgggtggtg tgagtagggg gatgaatcag ggaggggggcg ggggacccag ggggcaggag      420
ccacacaaag tctgtgcggg ggtgggagcg cacatagcaa ttggaaactg aaagcttatc      480
agaccctttc tggaaatcag cccactgttt ataaacttga ggccccaccc tcgagcgaga      540
taaccagggc tgaaagaggc ccgcctgggg gctggagaca tgcttgctgc ctgccctggc      600
gaaggattgg caggcttgcc cgtcacagga ccccgctgg ctgactcagg ggcgcaggcc       660
tcttgcgggg gagctggcct ccccgccccc acggccacgg gccgcccttt cctggcagga      720
cagcgggatc ttgcagctgt caggggaggg gaggcggggg ctgatgtcag gagggataca     780
aatagtgccg acggctgggg gccctgtctc ccctcgccgc atccactctc cggccggccg      840
cctgtccgcc gcctcctccg tgcgcccgcc agcctcgccc g                         881
```

<210> SEQ ID NO 11
<211> LENGTH: 1256
<212> TYPE: DNA
<213> ORGANISM: Artificial Sequence
<220> FEATURE:
<223> OTHER INFORMATION: Synthetic Construct

<400> SEQUENCE: 11

```
aaaatgcctt ctgagttgaa tatcaacact acaaaccgag tatctgcaga gggccctgcg        60
tatgagtgca agtgggtttt aggaccagga tgaggcgggg tggggtgcc tacctgacga       120
ccgaccccga cccactggac aagcacccaa ccccccattcc ccaaattgcg catcccctat     180
cagagagggg gaggggaaac aggatgcggc gaggcgcgtg cgcactgcca gcttcagcac      240
cgcggacagt gccttcgccc ccgcctggcg gcgcgcgcca ccgccgcctc agcactgaag      300
gcgcgctgac gtcactcgcc ggtccccgc aaactcccct tcccggccac cttggtcgcg       360
tccgcgccgc cgccgcccct aaaatgggca acattgcaa gcagcaaaca gcaaacacac       420
agccctccct gcctgctgac cttggagctg ggcagaggt cagagacctc tctgggccca      480
tgccacctcc aacatccact cgaccccttg gaatttcggt ggagaggagc agaggttgtc      540
ctggcgtggt ttaggtagtg tgagagggta ccccctgccc ccacagctc ctctcctgtg      600
ccttgtttcc cagccatgcg ttctcctcta taaatacccg ctctggtatt tggggttggc      660
agctgttgct gccagggaga tggttgggtt gacatgcggc tcctgacaaa acacaaaccc      720
ctggtgtgtg tgggcgtggg tggtgtgagt agggggatga atcagggagg gggcggggga      780
cccagggggc aggagccaca caaagtctgt gcggggtgg gagcgcacat agcaattgga     840
aactgaaagc ttatcagacc cttctggaa atcagcccac tgtttataaa cttgaggccc     900
caccctcgag cgagataacc agggctgaaa gaggcccgcc tggggggctgg agacatgctt    960
gctgcctgcc ctggcgaagg attggcaggc ttgcccgtca caggaccccc gctgctgac    1020
tcaggggcgc aggcctcttg cggggagct ggcctcccccg ccccacggc cacgggccgc    1080
```

```
ccttteetgg caggacagcg ggatettgca getgteaggg gaggggaggc gggggetgat      1140 gtcaggaggg atacaaatag tgccgacggc tgggggccct gtctccccte gccgcatcca      1200 ctctceggcc ggccgcctgt ccgccgcctc ctccgtgcgc cgccagcct cgcccg           1256
```

<210> SEQ ID NO 12
<211> LENGTH: 738
<212> TYPE: DNA
<213> ORGANISM: Artificial Sequence
<220> FEATURE:
<223> OTHER INFORMATION: Synthetic Construct

<400> SEQUENCE: 12

```
cccctaaaat gggcaaacat tgcaagcagc aaacagcaaa cacacagccc tacccctgc       60 ccccacagc tcctctcctg tgccttgttt cccagccatg cgttctcctc tataaatacc       120
cgctctggta tttggggttg gcagctgttg ctgccaggga gatggttggg ttgacatgcg      180
gctcctgaca aaacacaaac ccctggtgtg tgtgggcgtg ggtggtgtga gtagggggat      240
gaatcaggga gggggcgggg gacccagggg gcaggagcca cacaaagtct gtgcgggggt     300
gggagcgcac atagcaattg gaaactgaaa gcttatcaga ccctttctgg aaatcagccc     360
actgtttata aacttgaggc cccacccctcg agcgagataa ccagggctga agaggcccg     420 cctgggggct ggagacatgc ttgctgcctg ccctggcgaa ggattggcag gcttgcccgt     480
cacaggaccc ccgctggctg actcaggggc gcaggcctct tgcggggag ctggcctccc     540 cgcccccacg gccacgggcc gcccttcct ggcaggacag cgggatcttg cagctgtcag     600
gggaggggag gcggggctg atgtcaggag ggatacaaat agtgccgacg gctgggggcc     660
ctgtctcccc tcgccgcatc cactctccgg ccggccgcct gtccgccgcc tcctccgtgc     720
gcccgccagc ctcgcccg                                                  738
```

<210> SEQ ID NO 13
<211> LENGTH: 256
<212> TYPE: DNA
<213> ORGANISM: Artificial Sequence
<220> FEATURE:
<223> OTHER INFORMATION: Synthetic Construct

<400> SEQUENCE: 13

```
gaatgactcc tttcggtaag tgcagtggaa gctgtacact gcccaggcaa agcgtccggg      60
cagcgtaggc gggcgactca gatcccagcc agtgcactta gccctgtttt gctcctccga     120
taactggggt gaccttggtt aatattcacc agcagcctcc cccgttgccc ctctggatcc     180
actgcttaaa tacggacgag gacagggccc tgtctcctca gcttcaggca ccaccactga    240
cctgggacag tgaatc                                                    256
```

<210> SEQ ID NO 14
<211> LENGTH: 952
<212> TYPE: PRT
<213> ORGANISM: Homo sapiens

<400> SEQUENCE: 14

Met Gly Val Arg His Pro Pro Cys Ser His Arg Leu Leu Ala Val Cys
1               5                   10                  15

Ala Leu Val Ser Leu Ala Thr Ala Ala Leu Leu Gly His Ile Leu Leu
                20                  25                  30

His Asp Phe Leu Leu Val Pro Arg Glu Leu Ser Gly Ser Ser Pro Val
            35                  40                  45

-continued

```
Leu Glu Glu Thr His Pro Ala His Gln Gln Gly Ala Ser Arg Pro Gly
 50                  55                  60

Pro Arg Asp Ala Gln Ala His Pro Gly Arg Pro Arg Ala Val Pro Thr
 65                  70                  75                  80

Gln Cys Asp Val Pro Pro Asn Ser Arg Phe Asp Cys Ala Pro Asp Lys
                 85                  90                  95

Ala Ile Thr Gln Glu Gln Cys Glu Ala Arg Gly Cys Cys Tyr Ile Pro
            100                 105                 110

Ala Lys Gln Gly Leu Gln Gly Ala Gln Met Gly Gln Pro Trp Cys Phe
            115                 120                 125

Phe Pro Pro Ser Tyr Pro Ser Tyr Lys Leu Glu Asn Leu Ser Ser Ser
130                 135                 140

Glu Met Gly Tyr Thr Ala Thr Leu Thr Arg Thr Thr Pro Thr Phe Phe
145                 150                 155                 160

Pro Lys Asp Ile Leu Thr Leu Arg Leu Asp Val Met Met Glu Thr Glu
                165                 170                 175

Asn Arg Leu His Phe Thr Ile Lys Asp Pro Ala Asn Arg Arg Tyr Glu
            180                 185                 190

Val Pro Leu Glu Thr Pro His Val His Ser Arg Ala Pro Ser Pro Leu
195                 200                 205

Tyr Ser Val Glu Phe Ser Glu Glu Pro Phe Gly Val Ile Val Arg Arg
210                 215                 220

Gln Leu Asp Gly Arg Val Leu Leu Asn Thr Thr Val Ala Pro Leu Phe
225                 230                 235                 240

Phe Ala Asp Gln Phe Leu Gln Leu Ser Thr Ser Leu Pro Ser Gln Tyr
                245                 250                 255

Ile Thr Gly Leu Ala Glu His Leu Ser Pro Leu Met Leu Ser Thr Ser
            260                 265                 270

Trp Thr Arg Ile Thr Leu Trp Asn Arg Asp Leu Ala Pro Thr Pro Gly
            275                 280                 285

Ala Asn Leu Tyr Gly Ser His Pro Phe Tyr Leu Ala Leu Glu Asp Gly
290                 295                 300

Gly Ser Ala His Gly Val Phe Leu Leu Asn Ser Asn Ala Met Asp Val
305                 310                 315                 320

Val Leu Gln Pro Ser Pro Ala Leu Ser Trp Arg Ser Thr Gly Gly Ile
                325                 330                 335

Leu Asp Val Tyr Ile Phe Leu Gly Pro Glu Pro Lys Ser Val Val Gln
            340                 345                 350

Gln Tyr Leu Asp Val Val Gly Tyr Pro Phe Met Pro Pro Tyr Trp Gly
            355                 360                 365

Leu Gly Phe His Leu Cys Arg Trp Gly Tyr Ser Ser Thr Ala Ile Thr
370                 375                 380

Arg Gln Val Val Glu Asn Met Thr Arg Ala His Phe Pro Leu Asp Val
385                 390                 395                 400

Gln Trp Asn Asp Leu Asp Tyr Met Asp Ser Arg Arg Asp Phe Thr Phe
                405                 410                 415

Asn Lys Asp Gly Phe Arg Asp Phe Pro Ala Met Val Gln Glu Leu His
            420                 425                 430

Gln Gly Gly Arg Arg Tyr Met Met Ile Val Asp Pro Ala Ile Ser Ser
            435                 440                 445

Ser Gly Pro Ala Gly Ser Tyr Arg Pro Tyr Asp Glu Gly Leu Arg Arg
450                 455                 460
```

```
Gly Val Phe Ile Thr Asn Glu Thr Gly Gln Pro Leu Ile Gly Lys Val
465                 470                 475                 480

Trp Pro Gly Ser Thr Ala Phe Pro Asp Phe Thr Asn Pro Thr Ala Leu
                485                 490                 495

Ala Trp Trp Glu Asp Met Val Ala Glu Phe His Asp Gln Val Pro Phe
                500                 505                 510

Asp Gly Met Trp Ile Asp Met Asn Glu Pro Ser Asn Phe Ile Arg Gly
                515                 520                 525

Ser Glu Asp Gly Cys Pro Asn Asn Glu Leu Glu Asn Pro Pro Tyr Val
530                 535                 540

Pro Gly Val Val Gly Gly Thr Leu Gln Ala Ala Thr Ile Cys Ala Ser
545                 550                 555                 560

Ser His Gln Phe Leu Ser Thr His Tyr Asn Leu His Asn Leu Tyr Gly
                565                 570                 575

Leu Thr Glu Ala Ile Ala Ser His Arg Ala Leu Val Lys Ala Arg Gly
                580                 585                 590

Thr Arg Pro Phe Val Ile Ser Arg Ser Thr Phe Ala Gly His Gly Arg
                595                 600                 605

Tyr Ala Gly His Trp Thr Gly Asp Val Trp Ser Ser Trp Glu Gln Leu
610                 615                 620

Ala Ser Ser Val Pro Glu Ile Leu Gln Phe Asn Leu Leu Gly Val Pro
625                 630                 635                 640

Leu Val Gly Ala Asp Val Cys Gly Phe Leu Gly Asn Thr Ser Glu Glu
                645                 650                 655

Leu Cys Val Arg Trp Thr Gln Leu Gly Ala Phe Tyr Pro Phe Met Arg
                660                 665                 670

Asn His Asn Ser Leu Leu Ser Leu Pro Gln Glu Pro Tyr Ser Phe Ser
                675                 680                 685

Glu Pro Ala Gln Gln Ala Met Arg Lys Ala Leu Thr Leu Arg Tyr Ala
690                 695                 700

Leu Leu Pro His Leu Tyr Thr Leu Phe His Gln Ala His Val Ala Gly
705                 710                 715                 720

Glu Thr Val Ala Arg Pro Leu Phe Leu Glu Phe Pro Lys Asp Ser Ser
                725                 730                 735

Thr Trp Thr Val Asp His Gln Leu Leu Trp Gly Glu Ala Leu Leu Ile
                740                 745                 750

Thr Pro Val Leu Gln Ala Gly Lys Ala Glu Val Thr Gly Tyr Phe Pro
                755                 760                 765

Leu Gly Thr Trp Tyr Asp Leu Gln Thr Val Pro Val Glu Ala Leu Gly
                770                 775                 780

Ser Leu Pro Pro Pro Ala Ala Pro Arg Glu Pro Ala Ile His Ser
785                 790                 795                 800

Glu Gly Gln Trp Val Thr Leu Pro Ala Pro Leu Asp Thr Ile Asn Val
                805                 810                 815

His Leu Arg Ala Gly Tyr Ile Ile Pro Leu Gln Gly Pro Gly Leu Thr
                820                 825                 830

Thr Thr Glu Ser Arg Gln Gln Pro Met Ala Leu Ala Val Ala Leu Thr
                835                 840                 845

Lys Gly Gly Glu Ala Arg Gly Glu Leu Phe Trp Asp Asp Gly Glu Ser
850                 855                 860

Leu Glu Val Leu Glu Arg Gly Ala Tyr Thr Gln Val Ile Phe Leu Ala
865                 870                 875                 880
```

```
Arg Asn Asn Thr Ile Val Asn Glu Leu Val Arg Val Thr Ser Glu Gly
                885             890             895

Ala Gly Leu Gln Leu Gln Lys Val Thr Val Leu Gly Val Ala Thr Ala
            900             905             910

Pro Gln Gln Val Leu Ser Asn Gly Val Pro Val Ser Asn Phe Thr Tyr
        915             920             925

Ser Pro Asp Thr Lys Val Leu Asp Ile Cys Val Ser Leu Leu Met Gly
    930             935             940

Glu Gln Phe Leu Val Ser Trp Cys
945             950
```

TRANSCRIPTION REGULATORY ELEMENTS AND USES THEREOF

SEQUENCE LISTING

The instant application contains a Sequence Listing which has been submitted electronically in ASCII format and is hereby incorporated by reference in its entirety. Said ASCII copy, created Jul. 29, 2020, is named 51037-038002_Sequence_Listing_7.29.20_ST25, and is 19,076 bytes in size.

FIELD OF THE INVENTION

The invention relates to the field of nucleic acid biotechnology and provides compositions and methods for promoting the expression of a gene of interest.

BACKGROUND OF THE INVENTION

Pompe disease is a lysosomal storage disorder caused by mutations in the acid alpha-glucosidase (GAA) gene, which encodes an enzyme responsible for processing lysosomal glycogen. Patients with Pompe disease exhibit clinical phenotypes across a variety of tissues, including glycogen buildup in cells, deficits in cardiac, respiratory, and skeletal muscle function, and central nervous system pathology. Some of these deficits are significantly ameliorated by enzyme replacement therapy (ERT) using recombinant human GAA (rhGAA). Clinical efficacy has been limited by the immunogenicity of hGAA ERT and the lack of uptake of rhGAA into some affected tissues. Gene therapy has also been investigated as a potential therapeutic paradigm for this disease. The development of gene therapies for the treatment of Pompe have been hindered by the difficulty associate with achieving expression of therapeutically effective amounts of GAA in affected tissues while preventing the immune system from mounting an anti-GAA immune response. There remains a need for transcription regulatory elements capable of achieving this balance.

SUMMARY OF THE INVENTION

The invention provides compositions and methods for promoting the expression of a gene of interest, such as acid alpha-glucosidase (GAA), in cells of certain tissues, including those affected by Pompe disease. The compositions and methods described herein relate to nucleic acid regulatory elements that stimulate transcription of a transgene, such as GAA, in muscle cells (e.g., cardiac muscle cells), liver cells, and/or cells of the central nervous system. The nucleic acid regulatory elements described herein may be operably linked to a transgene, such as GAA, and may be administered to a patient (e.g., a human patient) for the treatment of a lysosomal storage disorder, such as Pompe disease. Advantageously, the compositions and methods described herein can be used to promote expression of GAA in patients, such as those that have Pompe disease, in the muscle cells and/or neurons that are affected by lysosomal storage disorders, and may simultaneously stimulate expression in the liver. This provides a surprising therapeutic benefit. Without being limited by mechanism, the present disclosure is based, in part, on the discovery that the transcription regulatory elements described herein may (i) promote expression of a transgene in cells affected by lysosomal storage disorders to ameliorate the pathology and (ii) stimulate expression in the liver, which serves to promote immune tolerance. The compositions and methods described herein can, thus, be used to treat lysosomal storage disorders, such as Pompe disease, in a manner that alleviates the deleterious effects of a lysosomal enzyme deficiency (e.g., a GAA deficiency) in patients while preventing or diminishing the mounting of an immune response against an enzyme introduced by gene therapy.

In a first aspect, the invention features a nucleic acid regulatory element containing a first segment operably linked to a second segment, wherein the first segment contains an apolipoprotein E hepatic control region (ApoE-HCR), or a functional portion thereof, and the second segment contains a desmin promoter, or a functional portion thereof. The 3' end of the first segment may be operably linked to the 5' end of the second segment. In some embodiments, the 5' end of the first segment is operably linked to the 3' end of the second segment.

In some embodiments, the first segment contains an ApoE-HCR enhancer having a nucleic acid sequence that is at least 85% identical (e.g., 85%, 86%, 87%, 88%, 89%, 90%, 91%, 92%, 93%, 94%, 95%, 96%, 97%, 98%, 99%, 99.9%, or 100% identical) to the nucleic acid sequence of SEQ ID NO: 3, or a functional portion thereof having a nucleic acid sequence that is at least 85% identical (e.g., 85%, 86%, 87%, 88%, 89%, 90%, 91%, 92%, 93%, 94%, 95%, 96%, 97%, 98%, 99%, 99.9%, or 100% identical) to the nucleic acid sequence of SEQ ID NO: 4. In some embodiments, the first segment contains an ApoE-HCR enhancer having a nucleic acid sequence that is at least 90% to the nucleic acid sequence of SEQ ID NO: 3, or a functional portion thereof having a nucleic acid sequence that is at least 90% identical to the nucleic acid sequence of SEQ ID NO: 4. In some embodiments, the first segment contains an ApoE-HCR enhancer having a nucleic acid sequence that is at least 95% to the nucleic acid sequence of SEQ ID NO: 3, or a functional portion thereof having a nucleic acid sequence that is at least 95% identical to the nucleic acid sequence of SEQ ID NO: 4. In some embodiments, the first segment contains an ApoE-HCR enhancer having the nucleic acid sequence of SEQ ID NO: 3, or a functional portion having the nucleic acid sequence of SEQ ID NO: 4.

In some embodiments, the first segment contains an ApoE-HCR enhancer having a nucleic acid sequence that is at least 85% identical (e.g., 85%, 86%, 87%, 88%, 89%, 90%, 91%, 92%, 93%, 94%, 95%, 96%, 97%, 98%, 99%, 99.9%, or 100% identical) to the nucleic acid sequence of SEQ ID NO: 3, or a functional portion thereof having a nucleic acid sequence that is at least 85% identical (e.g., 85%, 86%, 87%, 88%, 89%, 90%, 91%, 92%, 93%, 94%, 95%, 96%, 97%, 98%, 99%, 99.9%, or 100% identical) to the nucleic acid sequence of SEQ ID NO: 1. In some embodiments, the first segment contains an ApoE-HCR enhancer having a nucleic acid sequence that is at least 90% to the nucleic acid sequence of SEQ ID NO: 3, or a functional portion thereof having a nucleic acid sequence that is at least 90% identical to the nucleic acid sequence of SEQ ID NO: 1. In some embodiments, the first segment contains an ApoE-HCR enhancer having a nucleic acid sequence that is at least 95% to the nucleic acid sequence of SEQ ID NO: 3, or a functional portion thereof having a nucleic acid sequence that is at least 95% identical to the nucleic acid sequence of SEQ ID NO: 1. In some embodiments, the first segment contains an ApoE-HCR enhancer having the nucleic acid sequence of SEQ ID NO: 3, or a functional portion thereof having the nucleic acid sequence of SEQ ID NO: 1.

In some embodiments, the first segment contains an ApoE-HCR enhancer having a nucleic acid sequence that is at least 85% identical (e.g., 85%, 86%, 87%, 88%, 89%, 90%, 91%, 92%, 93%, 94%, 95%, 96%, 97%, 98%, 99%, 99.9%, or 100% identical) to the nucleic acid sequence of SEQ ID NO: 3, or a functional portion thereof having a nucleic acid sequence that is at least 85% identical (e.g., 85%, 86%, 87%, 88%, 89%, 90%, 91%, 92%, 93%, 94%, 95%, 96%, 97%, 98%, 99%, 99.9%, or 100% identical) to the nucleic acid sequence of SEQ ID NO: 2. In some embodiments, the first segment contains an ApoE-HCR enhancer having a nucleic acid sequence that is at least 90% to the nucleic acid sequence of SEQ ID NO: 3, or a functional portion thereof having a nucleic acid sequence that is at least 90% identical to the nucleic acid sequence of SEQ ID NO: 2. In some embodiments, the first segment contains an ApoE-HCR enhancer having a nucleic acid sequence that is at least 95% to the nucleic acid sequence of SEQ ID NO: 3, or a functional portion thereof having a nucleic acid sequence that is at least 95% identical to the nucleic acid sequence of SEQ ID NO: 2. In some embodiments, the first segment contains an ApoE-HCR enhancer having the nucleic acid sequence of SEQ ID NO: 3, or a functional portion thereof having the nucleic acid sequence of SEQ ID NO: 2.

In some embodiments, the first segment has a nucleic acid sequence that is at least 85% identical (e.g., 85%, 86%, 87%, 88%, 89%, 90%, 91%, 92%, 93%, 94%, 95%, 96%, 97%, 98%, 99%, 99.9%, or 100% identical) to the nucleic acid sequence of SEQ ID NO: 4. In some embodiments, the first segment has a nucleic acid sequence that is at least 90% identical to the nucleic acid sequence of SEQ ID NO: 4. In some embodiments, the first segment has a nucleic acid sequence that is at least 95% identical to the nucleic acid sequence of SEQ ID NO: 4. In some embodiments, the first segment has a nucleic acid sequence that is at least 95% identical to the nucleic acid sequence of SEQ ID NO: 4. For example, the first segment may contain the nucleic acid set forth in SEQ ID NO: 4.

In some embodiments, the first segment has a nucleic acid sequence that is at least 85% identical (e.g., 85%, 86%, 87%, 88%, 89%, 90%, 91%, 92%, 93%, 94%, 95%, 96%, 97%, 98%, 99%, 99.9%, or 100% identical) to the nucleic acid sequence of SEQ ID NO: 1. In some embodiments, the first segment has a nucleic acid sequence that is at least 90% identical to the nucleic acid sequence of SEQ ID NO: 1. In some embodiments, the first segment has a nucleic acid sequence that is at least 95% identical to the nucleic acid sequence of SEQ ID NO: 1. For example, the first segment may have the nucleic acid sequence of SEQ ID NO: 1.

In some embodiments, the first segment has a nucleic acid sequence that is at least 85% identical (e.g., 85%, 86%, 87%, 88%, 89%, 90%, 91%, 92%, 93%, 94%, 95%, 96%, 97%, 98%, 99%, 99.9%, or 100% identical) to the nucleic acid sequence of SEQ ID NO: 2. The first segment may have a nucleic acid sequence that is at least 90% identical to the nucleic acid sequence of SEQ ID NO: 2. In some embodiments, the first segment has a nucleic acid sequence that is at least 95% identical to the nucleic acid sequence of SEQ ID NO: 2. For example, the first segment may have the nucleic acid sequence of SEQ ID NO: 2.

In some embodiments, the first segment has a nucleic acid sequence that is at least 85% identical (e.g., 85%, 86%, 87%, 88%, 89%, 90%, 91%, 92%, 93%, 94%, 95%, 96%, 97%, 98%, 99%, 99.9%, or 100% identical) to the nucleic acid sequence of SEQ ID NO: 3. The first segment may have a nucleic acid sequence that is at least 90% identical to the nucleic acid sequence of SEQ ID NO: 3. In some embodiments, the first segment has a nucleic acid sequence that is at least 95% identical to the nucleic acid sequence of SEQ ID NO: 3. For example, the first segment may have the nucleic acid sequence of SEQ ID NO: 3.

In some embodiments, the second segment contains a 5' region having a nucleic acid sequence that is at least 85% identical (e.g., 85%, 86%, 87%, 88%, 89%, 90%, 91%, 92%, 93%, 94%, 95%, 96%, 97%, 98%, 99%, 99.9%, or 100% identical) to the nucleic acid sequence of SEQ ID NO: 5. In some embodiments, the 5' region has a nucleic acid sequence that is at least 90% identical to the nucleic acid sequence of SEQ ID NO: 5. In some embodiments, the 5' region has a nucleic acid sequence that is at least 95% identical to the nucleic acid sequence of SEQ ID NO: 5. For example, the 5' region may have the nucleic acid sequence of SEQ ID NO: 5.

In some embodiments, the second segment may contain a 3' region having a nucleic acid sequence that is at least 85% identical (e.g., 85%, 86%, 87%, 88%, 89%, 90%, 91%, 92%, 93%, 94%, 95%, 96%, 97%, 98%, 99%, 99.9%, or 100% identical) to the nucleic acid sequence of SEQ ID NO: 6. In some embodiments, the 3' region has a nucleic acid sequence that is at least 90% identical to the nucleic acid sequence of SEQ ID NO: 6. In some embodiments, the 3' region has a nucleic acid sequence that is at least 95% identical to the nucleic acid sequence of SEQ ID NO: 6. For example, the 3' region may have the nucleic acid sequence of SEQ ID NO: 6.

In some embodiments, the second segment has a nucleic acid sequence that is at least 85% identical (e.g., 85%, 86%, 87%, 88%, 89%, 90%, 91%, 92%, 93%, 94%, 95%, 96%, 97%, 98%, 99%, 99.9%, or 100% identical) to the nucleic acid sequence of SEQ ID NO: 7. In some embodiments, the second segment has a nucleic acid sequence that is at least 90% identical to the nucleic acid sequence of SEQ ID NO: 7. In some embodiments, the second segment has a nucleic acid sequence that is at least 95% identical to the nucleic acid sequence of SEQ ID NO: 7. For example, the 3' region may have the nucleic acid sequence of SEQ ID NO: 7.

In some embodiments, the nucleic acid regulatory element has a nucleic acid sequence that is at least 85% identical (e.g., 85%, 86%, 87%, 88%, 89%, 90%, 91%, 92%, 93%, 94%, 95%, 96%, 97%, 98%, 99%, 99.9%, or 100% identical) to the nucleic acid sequence of SEQ ID NO: 10. In some embodiments, the nucleic acid regulatory element has a nucleic acid sequence that is at least 90% identical to the nucleic acid sequence of SEQ ID NO: 10. In some embodiments, the nucleic acid regulatory element has a nucleic acid sequence that is at least 95% identical to the nucleic acid sequence of SEQ ID NO: 10.

For example, the nucleic acid regulatory element may have the nucleic acid sequence of SEQ ID NO: 10. In some embodiments, the nucleic acid regulatory element has a nucleic acid sequence that is at least 85% identical (e.g., 85%, 86%, 87%, 88%, 89%, 90%, 91%, 92%, 93%, 94%, 95%, 96%, 97%, 98%, 99%, 99.9%, or 100% identical) to the nucleic acid sequence of SEQ ID NO: 12. In some embodiments, the nucleic acid regulatory element has a nucleic acid sequence that is at least 90% identical to the nucleic acid sequence of SEQ ID NO: 12. In some embodiments, the nucleic acid regulatory element has a nucleic acid sequence that is at least 95% identical to the nucleic acid sequence of SEQ ID NO: 12. For example, the nucleic acid regulatory element may have the nucleic acid sequence of SEQ ID NO: 12.

In some embodiments, the nucleic acid regulatory element further includes a third segment that is positioned 5' or 3' with respect to the first and second segments. The third segment may be operably linked to the first and second segments.

In some embodiments, the third segment contains a promoter that stimulates expression of a transgene operably linked thereto in a cell of the central nervous system, such as a neuron, glial cell, or astrocyte, among others. In some embodiments, the third segment contains a promoter selected from the synapsin promoter, glial fibrillary acidic protein (GFAP) promoter, calcium/calmodulin-dependent protein kinase III promoter, tubulin alpha I promoter, microtubulin-associated protein IB (MAP IB) promoter, neuron-specific enolase promoter, platelet-derived growth factor beta chain promoter, neurofilament light chain promoter, neuron-specific VGF gene promoter, neuronal nuclei (NeuN) promoter, adenomatous polyposis coli (APC) promoter, ionized calcium-binding adapter molecule 1 (Iba-1) promoter, and the homeobox protein 9 (HB9) promoter, or a variant thereof (e.g., a variant having at least 85% sequence identity (for example, 85%, 86%, 87%, 88%, 89%, 90%, 91%, 92%, 93%, 94%, 95%, 96%, 97%, 98%, 99%, 99.9%, or more, sequence identity) to the nucleic acid sequence of the wild-type promoter locus and that is able to stimulate transcription of a transgene operably linked thereto upon introduction into a cell of the central nervous system) or functional portion thereof.

In some embodiments, the third segment contains a promoter that stimulates expression of a transgene operably linked thereto in a neuron. In some embodiments, the third segment contains a synapsin promoter, or a functional portion thereof.

In some embodiments, the third segment has a nucleic acid sequence that is at least 85% identical (e.g., 85%, 86%, 87%, 88%, 89%, 90%, 91%, 92%, 93%, 94%, 95%, 96%, 97%, 98%, 99%, 99.9%, or 100% identical) to the nucleic acid sequence of SEQ ID NO: 8. In some embodiments, the third segment has a nucleic acid sequence that is at least 90% identical to the nucleic acid sequence of SEQ ID NO: 8. In some embodiments, the third segment has a nucleic acid sequence that is at least 95% identical to the nucleic acid sequence of SEQ ID NO: 8. In some embodiments, the third segment has the nucleic acid sequence of SEQ ID NO: 8.

In some embodiments, the nucleic acid regulatory element has a nucleic acid sequence that is at least 85% identical (e.g., 85%, 86%, 87%, 88%, 89%, 90%, 91%, 92%, 93%, 94%, 95%, 96%, 97%, 98%, 99%, 99.9%, or 100% identical) to the nucleic acid sequence of SEQ ID NO: 11. In some embodiments, the nucleic acid regulatory element has a nucleic acid sequence that is at least 90% identical to the nucleic acid sequence of SEQ ID NO: 11. In some embodiments, the nucleic acid regulatory element has a nucleic acid sequence that is at least 95% identical to the nucleic acid sequence of SEQ ID NO: 11. For example, the nucleic acid regulatory element may have the nucleic acid sequence of SEQ ID NO: 11.

In another aspect, the invention features a nucleic acid regulatory element containing a first segment operably linked to a second segment, wherein the first segment contains a desmin promoter, or a functional portion thereof, and the second segment contains a promoter, or a functional portion thereof, that stimulates expression of a transgene operably linked thereto in a cell of the central nervous system, such as a neuron, glial cell, or astrocyte, among others. In some embodiments, the second segment contains a promoter selected from the synapsin promoter, GFAP promoter, calcium/calmodulin-dependent protein kinase III promoter, tubulin alpha I promoter, MAP IB promoter, neuron-specific enolase promoter, platelet-derived growth factor beta chain promoter, neurofilament light chain promoter, neuron-specific VGF gene promoter, NeuN promoter, APC promoter, Iba-1 promoter, and the HB9 promoter, or a variant thereof (e.g., a variant having at least 85% sequence identity (for example, 85%, 86%, 87%, 88%, 89%, 90%, 91%, 92%, 93%, 94%, 95%, 96%, 97%, 98%, 99%, 99.9%, or more, sequence identity) to the nucleic acid sequence of the wild-type promoter locus and that is able to stimulate transcription of a transgene operably linked thereto upon introduction into a cell of the central nervous system) or functional portion thereof.

In some embodiments, the second segment contains a promoter that stimulates expression of a transgene operably linked thereto in a neuron. In some embodiments, the second segment contains a synapsin promoter, or a functional portion thereof.

In some embodiments, the 3' end of the first segment is operably linked to the 5' end of the second segment. In some embodiments, the 5' end of the first segment is operably linked to the 3' end of the second segment.

In some embodiments, the first segment contains a 5' region having a nucleic acid sequence that is at least 85% identical (e.g., 85%, 86%, 87%, 88%, 89%, 90%, 91%, 92%, 93%, 94%, 95%, 96%, 97%, 98%, 99%, 99.9%, or 100% identical) to the nucleic acid sequence of SEQ ID NO: 5. In some embodiments, the 5' region has a nucleic acid sequence that is at least 90% identical to the nucleic acid sequence of SEQ ID NO: 5. In some embodiments, the 5' region has a nucleic acid sequence that is at least 95% identical to the nucleic acid sequence of SEQ ID NO: 5. For example, the 5' region may have the nucleic acid sequence of SEQ ID NO: 5.

In some embodiments, the first segment contains a 3' region having a nucleic acid sequence that is at least 85% identical (e.g., 85%, 86%, 87%, 88%, 89%, 90%, 91%, 92%, 93%, 94%, 95%, 96%, 97%, 98%, 99%, 99.9%, or 100% identical) to the nucleic acid sequence of SEQ ID NO: 6. In some embodiments, the 3' region has a nucleic acid sequence that is at least 90% identical to the nucleic acid sequence of SEQ ID NO: 6. In some embodiments, the 3' region has a nucleic acid sequence that is at least 95% identical to the nucleic acid sequence of SEQ ID NO: 6. For example, the 3' region may have the nucleic acid sequence of SEQ ID NO: 6.

In some embodiments, the first segment has a nucleic acid sequence that is at least 85% identical (e.g., 85%, 86%, 87%, 88%, 89%, 90%, 91%, 92%, 93%, 94%, 95%, 96%, 97%, 98%, 99%, 99.9%, or 100% identical) to the nucleic acid sequence of SEQ ID NO: 7. In some embodiments, the first segment has a nucleic acid sequence that is at least 90% identical to the nucleic acid sequence of SEQ ID NO: 7. In some embodiments, the first segment has a nucleic acid sequence that is at least 95% identical to the nucleic acid sequence of SEQ ID NO: 7. For example, the first segment may have the nucleic acid sequence of SEQ ID NO: 7.

In some embodiments, the second segment has a nucleic acid sequence that is at least 85% identical (e.g., 85%, 86%, 87%, 88%, 89%, 90%, 91%, 92%, 93%, 94%, 95%, 96%, 97%, 98%, 99%, 99.9%, or 100% identical) to the nucleic acid sequence of SEQ ID NO: 8. In some embodiments, the second segment has a nucleic acid sequence that is at least 90% identical to the nucleic acid sequence of SEQ ID NO: 8. In some embodiments, the second segment has a nucleic acid sequence that is at least 95% identical to the nucleic acid sequence of SEQ ID NO: 8. In some embodiments, the second segment has the nucleic acid sequence of SEQ ID NO: 8.

In another aspect, the invention features a vector containing the nucleic acid regulatory element of any of the foregoing aspects or embodiments thereof. The nucleic acid regulatory element may be operably linked to a transgene, and may induce expression of the transgene upon introduction of the vector into a cell (e.g., a mammalian cell, such as a human cell). The cell may be, for example, a muscle cell (e.g., a cardiac muscle cell or a skeletal muscle cell), a neuron, or a hepatocyte. In some embodiments, the transgene encodes a lysosomal enzyme, such as GAA. In some embodiments, the vector is a viral vector, such as an adeno-associated virus (AAV), adenovirus, lentivirus, retrovirus, poxvirus, baculovirus, herpes simplex virus, or vaccinia virus. In some embodiments, the viral vector is an AAV, such as an AAV1, AAV2, AAV3, AAV4, AAV5, AAV6, AAV7, AAV8, AAV9, or AAVrh74 serotype. The viral vector may be a pseudotyped AAV, such as a recombinant AAV (rAAV) 2/8 or rAAV2/9.

In another aspect, the invention features a composition containing the nucleic acid regulatory element of any of the above aspects or embodiments thereof. The composition may be, for example, a liposome, vesicle, synthetic vesicle, exosome, synthetic exosome, dendrimer, or nanoparticle. In the composition, the nucleic acid regulatory element may be operably linked to a transgene (e.g., a transgene encoding a lysosomal enzyme, such as GAA).

In yet another aspect, the invention features a method of expressing a transgene in a cell by contacting the cell with the vector or composition of any of the foregoing aspects or embodiments thereof for a time sufficient to simulate transcription of the transgene in the cell.

In another aspect, the invention features a method of treating a lysosomal storage disease, such as Pompe disease, in a patient (e.g., a mammalian patient, such as a human patient) in need thereof by administering to the patient a therapeutically effective amount of a vector or composition described herein.

In yet another aspect, the invention features a kit containing a vector or composition described herein. The kit may contain a package insert, for example, that instructs a user of the kit to contact the vector or composition with a cell (e.g., a mammalian cell, such as a human cell), thereby expressing a transgene operably linked to the regulatory element.

Definitions

As used herein, the term "about" refers to a value that is within 10% above or below the value being described.

As used herein, the term "ApoE-HCR enhancer" refers to the human apolipoprotein E hepatic control region, the nucleic acid sequence of which is set forth in SEQ ID NO: 3, as well as nucleic acids having at least 85% identity (e.g., 85%, 86% e.g., 85%, 86%, 87%, 88%, 89%, 90%, 91%, 92%, 93%, 94%, 95%, 96%, 97%, 98%, 99%, or 99.9% identity, or more) to the nucleic acid sequence of SEQ ID NO: 3 and that promote the expression of a transgene in a cell (e.g., a eukaryotic cell, such as a mammalian cell, human cell, or human liver cell) when the transgene is operably linked to the enhancer.

As used herein, the terms "conservative mutation," "conservative substitution," or "conservative amino acid substitution" refer to a substitution of one or more amino acids for one or more different amino acids that exhibit similar physicochemical properties, such as polarity, electrostatic charge, and steric volume. These properties are summarized for each of the twenty naturally-occurring amino acids in table 1 below.

TABLE 1

Representative physicochemical properties of naturally-occurring amino acids

| Amino Acid | 3 Letter Code | 1 Letter Code | Side-chain Polarity | Electrostatic character at physiological pH (7.4) | Steric Volume[†] |
|---|---|---|---|---|---|
| Alanine | Ala | A | nonpolar | neutral | small |
| Arginine | Arg | R | polar | cationic | large |
| Asparagine | Asn | N | polar | neutral | intermediate |
| Aspartic acid | Asp | D | polar | anionic | intermediate |
| Cysteine | Cys | C | nonpolar | neutral | intermediate |
| Glutamic acid | Glu | E | polar | anionic | intermediate |
| Glutamine | Gln | Q | polar | neutral | intermediate |
| Glycine | Gly | G | nonpolar | neutral | small |
| Histidine | His | H | polar | Both neutral and cationic forms in equilibrium at pH 7.4 | large |
| Isoleucine | Ile | I | nonpolar | neutral | large |
| Leucine | Leu | L | nonpolar | neutral | large |
| Lysine | Lys | K | polar | cationic | large |
| Methionine | Met | M | nonpolar | neutral | large |
| Phenylalanine | Phe | F | nonpolar | neutral | large |
| Proline | Pro | P | nonpolar | neutral | intermediate |
| Serine | Ser | S | polar | neutral | small |
| Threonine | Thr | T | polar | neutral | intermediate |
| Tryptophan | Trp | w | nonpolar | neutral | bulky |
| Tyrosine | Tyr | Y | polar | neutral | large |
| Valine | Val | V | nonpolar | neutral | intermediate |

[†]based on volume in $Å^3$: 50-100 is small, 100-150 is intermediate, 150-200 is large, and >200 is bulky From this table it is appreciated that the conservative amino acid families include, e.g., (i) G, A, V, L, I, P, and M; (ii) D and E; (iii) C, S and T; (iv) H, K and R; (v) N and Q; and (vi) F, Y and W. A conservative mutation or substitution is therefore one that substitutes one amino acid for a member of the same amino acid family (e.g., a substitution of Ser for Thr or Lys for Arg).

As used herein, the term "desmin promoter" refers to the nucleic acid set forth in SEQ ID NO: 7, as well as nucleic acids having at least 85% identity (e.g., 85%, 86% e.g., 85%, 86%, 87%, 88%, 89%, 90%, 91%, 92%, 93%, 94%, 95%, 96%, 97%, 98%, 99%, or 99.9% identity, or more) to the nucleic acid sequence of SEQ ID NO: 7 and that promote the expression of a transgene in a cell (e.g., a eukaryotic cell, such as a mammalian cell, human cell, or human muscle cell) when the transgene is operably linked to the enhancer.

As used herein in the context of a transcription regulatory element, the term "functional portion" refers to a portion of a larger nucleic acid that retains the ability to stimulate transcription of a gene of interest in a target cell. For example, the apolipoprotein E hepatic control region (ApoE-HCR) is a 774-nucleotide enhancer, the sequence of which is set forth in SEQ ID NO: 3. A portion of this locus that contains 193 nucleotides (the nucleic acid sequence of which is set forth in SEQ ID NO: 1) is able to retain the transcription-activating properties of the larger locus. The 193-nucleotide portion set forth in SEQ ID NO: 1 is, thus, a "functional portion" of the ApoE-HCR locus. As an additional example, another portion of the ApoE-HCR locus that is able to retain the transcription-activating properties of the full-length enhancer is the 320-nucleotide segment set forth in SEQ ID NO: 2. The 320-nucleotide portion set forth in SEQ ID NO: 2 is, thus, a "functional portion" of the ApoE-HCR locus. As a further example, another portion of the ApoE-HCR locus that is able to retain the transcription-activating properties of the full-length enhancer is the 50-nucleotide segment set forth in SEQ ID NO: 4. The 50-nucleotide portion set forth in SEQ ID NO: 4 is also, thus, a "functional portion" of the ApoE-HCR locus.

As used herein, the term "operably linked" refers to a first molecule joined to a second molecule, wherein the molecules are so arranged that the first molecule affects the function of the second molecule. The two molecules may or may not be part of a single contiguous molecule and may or may not be adjacent. For example, a promoter is operably linked to a transcribable polynucleotide molecule if the promoter modulates transcription of the transcribable polynucleotide molecule of interest in a cell. Additionally, two portions of a transcription regulatory element are operably linked to one another if they are joined such that the transcription-activating functionality of one portion is not adversely affected by the presence of the other portion. Two transcription regulatory elements may be operably linked to one another by way of a linker nucleic acid (e.g., an intervening non-coding nucleic acid) or may be operably linked to one another with no intervening nucleotides present.

"Percent (%) sequence identity" with respect to a reference polynucleotide or polypeptide sequence is defined as the percentage of nucleic acids or amino acids in a candidate sequence that are identical to the nucleic acids or amino acids in the reference polynucleotide or polypeptide sequence, after aligning the sequences and introducing gaps, if necessary, to achieve the maximum percent sequence identity. Alignment for purposes of determining percent nucleic acid or amino acid sequence identity can be achieved in various ways that are within the capabilities of one of skill in the art, for instance, using publicly available computer software such as BLAST, BLAST-2, or Megalign software. Those skilled in the art can determine appropriate parameters for aligning sequences, including any algorithms needed to achieve maximal alignment over the full length of the sequences being compared. For example, percent sequence identity values may be generated using the sequence comparison computer program BLAST. As an illustration, the percent sequence identity of a given nucleic acid or amino acid sequence, A, to, with, or against a given nucleic acid or amino acid sequence, B, (which can alternatively be phrased as a given nucleic acid or amino acid sequence, A that has a certain percent sequence identity to, with, or against a given nucleic acid or amino acid sequence, B) is calculated as follows:

100 multiplied by (the fraction X/Y)

where X is the number of nucleotides or amino acids scored as identical matches by a sequence alignment program (e.g., BLAST) in that program's alignment of A and B, and where Y is the total number of nucleic acids in B. It will be appreciated that where the length of nucleic acid or amino acid sequence A is not equal to the length of nucleic acid or amino acid sequence B, the percent sequence identity of A to B will not equal the percent sequence identity of B to A.

As used herein, the term "pharmaceutical composition" refers to a mixture containing a therapeutic compound to be administered to a subject, such as a mammal, e.g., a human, in order to prevent, treat or control a particular disease or condition affecting or that may affect the subject.

As used herein, the term "pharmaceutically acceptable" refers to those compounds, materials, compositions and/or dosage forms, which are suitable for contact with the tissues of a subject, such as a mammal (e.g., a human) without excessive toxicity, irritation, allergic response and other problem complications commensurate with a reasonable benefit/risk ratio.

As used herein, the term "sample" refers to a specimen (e.g., blood, blood component (e.g., serum or plasma), urine, saliva, amniotic fluid, cerebrospinal fluid, tissue (e.g., placental or dermal), pancreatic fluid, chorionic villus sample, or cells) isolated from a subject. The subject may be, for example, a patient suffering from a disease described herein, such as a lysosomal storage disorder (e.g., Pompe disease).

As used herein, the phrases "specifically binds" and "binds" refer to a binding reaction which is determinative of the presence of a particular molecule, such as a polypeptide, in a heterogeneous population of polypeptides and other biological molecules that is recognized, e.g., by a ligand, such as an antibody or antigen-binding fragment thereof, with particularity. A ligand (e.g., a complementary polynucleotide) that specifically binds to a protein may bind to the protein, e.g., with a $K_D$ of less than 100 nM. For example, a ligand that specifically binds to a protein may bind to the protein with a $K_D$ of up to 100 nM (e.g., between 1 pM and 100 nM). A ligand that does not exhibit specific binding to another molecule or a domain thereof may exhibit a $K_D$ of greater than 100 nM (e.g., greater than 200 nM, 300 nM, 400 nM, 500 nM, 600 nm, 700 nM, 800 nM, 900 nM, 1 μM, 100 μM, 500 μM, or 1 mM) for that particular molecule or domain thereof. A variety of assay formats may be used to determine the affinity of a ligand for a specific protein. For example, solid-phase ELISA assays are routinely used to identify ligands that specifically bind a target protein. See, e.g., Harlow & Lane, Antibodies, A Laboratory Manual, Cold Spring Harbor Press, New York (1988) and Harlow & Lane, Using Antibodies, A Laboratory Manual, Cold Spring Harbor Press, New York (1999), for a description of assay formats and conditions that can be used to determine specific protein binding.

As used herein, the terms "subject" and "patient" refer to an organism that receives treatment for a particular disease or condition as described herein (such as a lysosomal storage disorder, e.g., Pompe disease). Examples of subjects and patients include mammals, such as humans, receiving treatment for a disease or condition described herein.

As used herein, the term "synapsin promoter" refers to the nucleic acid set forth in SEQ ID NO: 8, and variants thereof having at least 85% identity (e.g., 85%, 86% e.g., 85%, 86%, 87%, 88%, 89%, 90%, 91%, 92%, 93%, 94%, 95%, 96%, 97%, 98%, 99%, or 99.9% identity, or more) to the nucleic acid sequence of SEQ ID NO: 8 and that promote the expression of a transgene in a cell (e.g., a eukaryotic cell, such as a mammalian cell, human cell, or human neuron) when the transgene is operably linked to the enhancer.

As used herein, the term "transcription regulatory element" refers to a nucleic acid that controls, at least in part, the transcription of a gene of interest. Transcription regulatory elements may include promoters, enhancers, and other nucleic acids (e.g., polyadenylation signals) that control or help to control gene transcription. Examples of transcription regulatory elements are described, for example, in Goeddel, Gene Expression Technology: Methods in Enzymology 185 (Academic Press, San Diego, CA, 1990).

As used herein, the terms "treat" or "treatment" refer to therapeutic treatment, in which the object is to prevent or slow down (lessen) an undesired physiological change or disorder, such as the progression of a lysosomal storage disorder, such as Pompe disease, among others. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. In the context of lysosomal storage disorders, such as Pompe disease, treatment of a patient may manifest in one or more detectable changes, such as an increase in the concentration of acid alpha-glucosidase (GAA) protein or nucleic acids (e.g., DNA or RNA, such as mRNA) encoding GAA, or an increase in GAA activity (e.g., by 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 100%, 200%, 300%, 400%, 500%, 600%, 700%, 800%, 900%, 10-fold, 20-fold, 30-fold, 40-fold, 50-fold, 60-fold, 70-fold, 80-fold, 90-fold, 100-fold, 500-fold, 1,000-fold, or more. The concentration of GAA protein may be determined using protein detection assays known in the art, including ELISA assays described herein. The concentration of GAA-encoding nucleic acids may be determined using nucleic acid detection assays (e.g., RNA Seq assays) described herein. Exemplary protocols for the detection of GAA proteins and nucleic acids are provided in Example 1, below. Additionally, treatment of a patient suffering from a lysosomal storage disorder, such as Pompe disease, may manifest in improvements in a patient's muscle function (e.g., cardiac or skeletal muscle function) as well as improvements in muscle coordination. Exemplary procedures for measuring muscle function are described in Example 1, below.

As used herein, the term "vector" refers to a nucleic acid, e.g., DNA or RNA, that may function as a vehicle for the delivery of a gene of interest into a cell (e.g., a mammalian cell, such as a human cell), such as for purposes of replication and/or expression. Exemplary vectors useful in conjunction with the compositions and methods described herein are plasmids, DNA vectors, RNA vectors, virions, or other suitable replicon (e.g., viral vector). A variety of vectors have been developed for the delivery of polynucleotides encoding exogenous proteins into a prokaryotic or eukaryotic cell. Examples of such expression vectors are disclosed in, e.g., WO 1994/11026, the disclosure of which is incorporated herein by reference. Expression vectors described herein contain a polynucleotide sequence as well as, e.g., additional sequence elements used for the expression of proteins and/or the integration of these polynucleotide sequences into the genome of a mammalian cell. Certain vectors that can be used for the expression of transgenes described herein include plasmids that contain regulatory sequences, such as promoter and enhancer regions, which direct gene transcription. Other useful vectors for expression of transgenes contain polynucleotide sequences that enhance the rate of translation of these genes or improve the stability or nuclear export of the mRNA that results from gene transcription. These sequence elements include, e.g., 5' and 3' untranslated regions, an internal ribosomal entry site (IRES), and polyadenylation signal site in order to direct efficient transcription of the gene carried on the expression vector. The expression vectors described herein may also contain a polynucleotide encoding a marker for selection of cells that contain such a vector. Examples of a suitable marker include genes that encode resistance to antibiotics, such as ampicillin, chloramphenicol, kanamycin, or nourseothricin.

DETAILED DESCRIPTION

Figure 1:
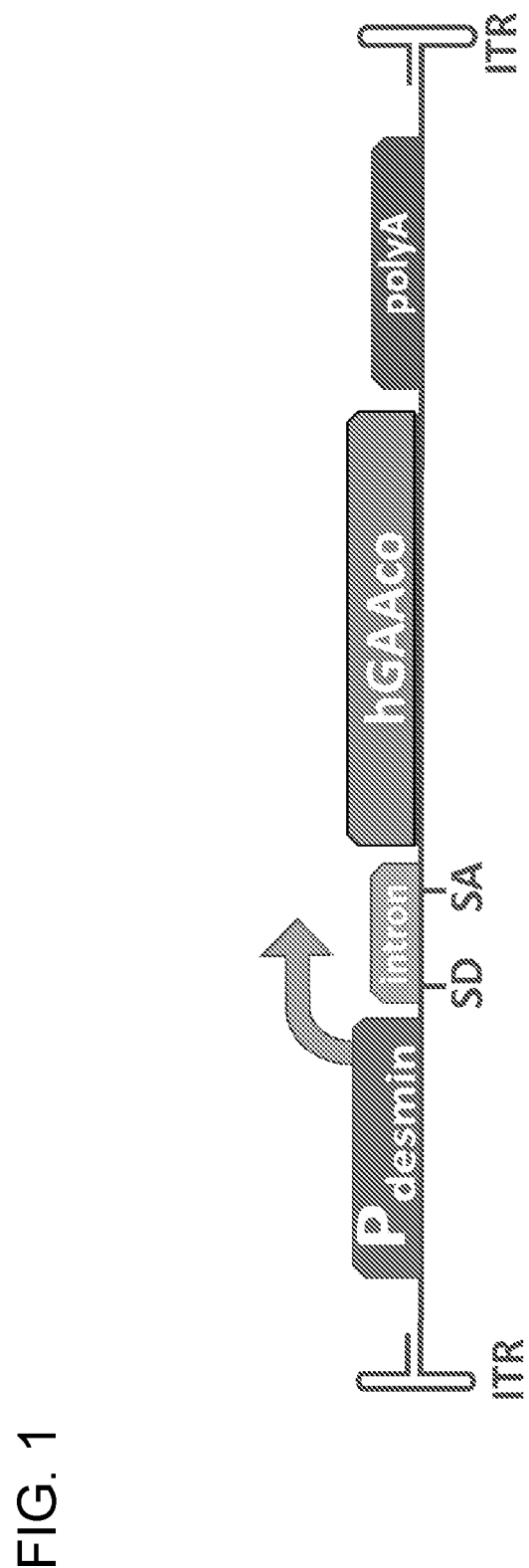
FIG. 1 is a diagram showing the arrangement of elements in various vectors. GAAco, human codon optimized acid alpha-glucosidase gene (GAA); ITR, inverted terminal repeat; SD, splice donor; SA; splice acceptor.

Described herein are transcription regulatory elements that stimulate transcription of a gene of interest, such as a gene encoding a lysosomal enzyme (e.g., acid alpha-glucosidase (GAA)), in cells of certain tissues. Particularly, the transcription regulatory elements described herein may promote expression of target lysosomal enzyme genes in tissues that are affected by lysosomal storage disorders, such as Pompe disease. Such tissues include muscle tissue (e.g., cardiac and skeletal muscle tissue) and central nervous system tissue. The nucleic acid regulatory elements described herein may be operably linked to a transgene, such as GAA, and incorporated into a vehicle for administration to a patient (e.g., a human patient) for the treatment of a lysosomal storage disorder, such as Pompe disease. The delivery vehicle may be a vector, such as a viral vector described herein, or other agent for introducing a nucleic acid into a cell of interest (e.g., a liposome, vesicle, exosome, dendrimer, or nanoparticle described herein).

The present invention is based, in part, on the discovery of nucleic acid regulatory elements that can be used to (i) promote expression of a transgene in cells affected by lysosomal storage disorders to ameliorate the pathology and (ii) stimulate expression in the liver, which serves to promote immune tolerance. The compositions and methods described herein can, thus, be used to treat lysosomal storage disorders, such as Pompe disease, so as to treat the deleterious effects on muscle tissue of a lysosomal enzyme deficiency (e.g., a GAA deficiency) while preventing or diminishing an immune response against the enzyme introduced (e.g., GAA).

The sections that follow provide a description of transcription regulatory elements exhibiting the foregoing advantageous properties. The following sections also describe various transgenes, viral vectors, and transfection agents that may be used in conjunction with the transcription regulatory elements described herein, as well as methods of using the compositions described herein for the treatment of various disorders.

Transcription Regulatory Elements

Transcription regulatory elements that may be used in conjunction with the compositions and methods described herein may contain various portions operably linked to one another. For example, transcription regulatory elements described herein may contain an apolipoprotein E hepatic control region (ApoE-HCR), as set forth in SEQ ID NO: 3, or a functional portion thereof. An exemplary functional portion of the ApoE-HCR is the 320-nucleotide portion set forth in SEQ ID NO: 2, which is described in Dang et al., J. Biol. Chem. 270:22577-22585 (1995), the disclosure of which is incorporated herein by reference as it pertains to the ApoE-HCR locus and functional portions thereof. Another example of an ApoE-HCR nucleic acid that may be used in conjunction with the compositions and methods described herein is a 193-nucleotide segment of the ApoE-HCR, the nucleic acid sequence of which is set forth in SEQ ID NO: 1. A further example of an ApoE-HCR nucleic acid that may be used in conjunction with the compositions and methods described herein is the 50-nucleotide segment set forth in SEQ ID NO: 4. Additional nucleic acid regulatory elements useful in conjunction with the compositions and methods described herein include nucleic acid molecules that have at least 85% sequence identity (e.g., 86%, 87%, 88%, 89%, 90%, 91%, 92%, 93%, 94%, 95%, 96%, 97%, 98%, 99%, 99.9%, or greater, sequence identity) with respect to the above nucleic acid sequences.

Additionally or alternatively, transcription regulatory elements described herein may contain a desmin promoter, or functional portion thereof. For example, the regulatory element may contain a desmin promoter that contains from nucleic acids −984 to −644, with respect to the desmin transcription start site, of the human desmin locus. The nucleic acid sequence of this construct is set forth in SEQ ID NO: 5. The regulatory element may contain a desmin promoter that contains from nucleic acids −269 to +76, with respect to the desmin transcription start site, of the human desmin locus. The nucleic acid sequence of this construct is set forth in SEQ ID NO: 6. The regulatory element may contain the nucleic acid of SEQ ID NO: 5 fused to the nucleic acid of SEQ ID NO: 6, with no intervening nucleic acids, to form a desmin promoter containing from nucleotide −984 to nucleotide −644 and from nucleotide −269 to nucleotide +76, with respect to the desmin transcription start site, of the human desmin locus. The nucleic acid sequence of this regulatory element is set forth in SEQ ID NO: 7. Additional nucleic acid regulatory elements useful in conjunction with the compositions and methods described herein include nucleic acid molecules that have at least 85% sequence identity (e.g., 86%, 87%, 88%, 89%, 90%, 91%, 92%, 93%, 94%, 95%, 96%, 97%, 98%, 99%, 99.9%, or greater, sequence identity) with respect to the above nucleic acid sequences.

Transcription regulatory elements that may be used in conjunction with the compositions and methods described herein include promoters that stimulates expression of a transgene operably linked thereto in a cell of the central nervous system, such as a neuron, glial cell, or astrocyte, among others. Examples of such promoters are the synapsin promoter, glial fibrillary acidic protein (GFAP) promoter, calcium/calmodulin-dependent protein kinase III promoter, tubulin alpha I promoter, microtubulin-associated protein IB (MAP IB) promoter, neuron-specific enolase promoter, platelet-derived growth factor beta chain promoter, neurofilament light chain promoter, neuron-specific VGF gene promoter, neuronal nuclei (NeuN) promoter, adenomatous polyposis coli (APC) promoter, ionized calcium-binding adapter molecule 1 (Iba-1), and the homeobox protein 9 (HB9) promoter, or a variant thereof (e.g., a variant having at least 85% sequence identity (for example, 85%, 86%, 87%, 88%, 89%, 90%, 91%, 92%, 93%, 94%, 95%, 96%, 97%, 98%, 99%, 99.9%, or more, sequence identity) to the nucleic acid sequence of the wild-type promoter locus and that is able to stimulate transcription of a transgene operably linked thereto upon introduction into a cell of the central nervous system) or functional portion thereof.

For example, transcription regulatory elements that may be used in conjunction with the compositions and methods described herein may contain a synapsin promoter, or functional portion thereof. An exemplary regulatory element containing a synapsin promoter region is set forth in SEQ ID NO: 8. This construct contains from nucleotide −465 to nucleotide −90, with respect to the synapsin transcription start site, of the human synapsin locus. Additional nucleic acid regulatory elements useful in conjunction with the compositions and methods described herein include nucleic acid molecules that have at least 85% sequence identity (e.g., 86%, 87%, 88%, 89%, 90%, 91%, 92%, 93%, 94%, 95%, 96%, 97%, 98%, 99%, 99.9%, or greater, sequence identity) with respect to this nucleic acid sequence.

The foregoing nucleic acid regulatory elements are summarized in Table 2, below.

TABLE 2

Exemplary nucleic acid regulatory elements

| SEQ ID NO. | Description of Transcription Regulatory Element | Nucleic Acid Sequence |
|---|---|---|
| 1 | 193-nucleotide segment of ApoE HCR locus | CCCCTAAAATGGGCAAACATTGCAAGCAG CAAACAGCAAACACACAGCCCTCCCTGCC TGCTGACCTTGGAGCTGGGGCAGAGGTC AGAGACCTCTCTGGGCCCATGCCACCTCC AACATCCACTCGACCCCTTGGAATTTCGG TGGAGAGGAGCAGAGGTTGTCCTGGCGT GGTTTAGGTAGTGTGAGAGGG |
| 2 | 320-nucleotide segment of ApoE-HCR locus | GGCTCAGAGGCACACAGGAGTTTCTGGG CTCACCCTGCCCCCTTCCAACCCCTCAGT TCCCATCCTCCAGCAGCTGTTTGTGTGCT GCCTCTGAAGTCCACACTGAACAAACTTC AGCCTACTCATGTCCCTAAAATGGGCAAA CATTGCAAGCAGCAAACAGCAAACACACA GCCCTCCCTGCCTGCTGACCTTGGAGCT GGGGCAGAGGTCAGAGACCTCTCTGGGC CCATGCCACCTCCAACATCCACTCGACCC CTTGGAATTTCGGTGGAGAGGAGCAGAG GTTGTCCTGGCGTGGTTTAGGTAGTGTGA GAGGG |
| 3 | Full-length ApoE-HCR locus | CTGCAGGCTCAGAGGCACACAGGAGTTT CTGGGCTCACCCTGCCCCCTTCCAACCCC TCAGTTCCCATCCTCCAGCAGCTGTTTGT GTGCTGCCTCTGAAGTCCACACTGAACAA ACTTCAGCCTACTCATGTCCCTAAAATGG GCAAACATTGCAAGCAGCAAACAGCAAAC ACACAGCCCTCCCTGCCTGCTGACCTTGG AGCTGGGGCAGAGGTCAGAGACCTCTCT GGGCCCATGCCACCTCCAACATCCACTCG ACCCCTTGGAATTTCGGTGGAGAGGAGCA GAGGTTGTCCTGGCGTGGTTTAGGTAGTG TGAGAGGGTCCGGGTTCAAAACCACTTGC TGGGTGGGGAGTCGTCAGTAAGTGGCTA TGCCCCGACCCCGAAGCCTGTTTCCCCAT CTGTACAATGGAAATGATAAAGACGCCCA TCTGATAGGGTTTTTGTGGCAAATAAACAT TTGGTTTTTTTGTTTTGTTTTGTTTTGTTTT TTGAGATGGAGGTTTGCTCTGTCGCCCAG GCTGGAGTGCAGTGACACAATCTCATCTC ACCACAACCTTCCCCTGCCTCAGCCTCCC AAGTAGCTGGGATTACAAGCATGTGCCAC CACACCTGGCTAATTTTCTATTTTTAGTAG AGACGGGTTTCTCCATGTTGGTCAGCCTC AGCCTCCCAAGTAACTGGGATTACAGGCC TGTGCCACCACACCCGGCTAATTTTTTCTA TTTTTGACAGGGACGGGGTTTCACCATGT TGGTCAGGCTGGTCTAGA |
| 4 | 50-nucleotide segment of ApoE-HCR locus | CCCCTAAAATGGGCAAACATTGCAAGCAG CAAACAGCAAACACACAGCCC |
| 5 | Segment of desmin promoter containing nucleotides −984 to −644 with respect to desmin transcription start site | TACCCCCTGCCCCCCACAGCTCCTCTCCT GTGCCTTGTTTCCCAGCCATGCGTTCTCC TCTATAAATACCCGCTCTGGTATTTGGGG TTGGCAGCTGTTGCTGCCAGGGAGATGG TTGGGTTGACATGCGGCTCCTGACAAAAC ACAAACCCTGGTGTGTGTGGGCGTGGG TGGTGTGAGTAGGGGGATGAATCAGGGA GGGGGCGGGGACCCAGGGGGCAGGAG CCACACAAAGTCTGTGCGGGGGTGGGAG |

TABLE 2-continued

Exemplary nucleic acid regulatory elements

| SEQ ID NO. | Description of Transcription Regulatory Element | Nucleic Acid Sequence |
|---|---|---|
| | | CGCACATAGCAATTGGAAACTGAAAGCTT ATCAGACCCTTTCTGGAAATCAGCCCACT GTTTATAAACTTGAGGCCCCACCCTCGAG |
| 6 | Segment of desmin promoter containing nucleotides −269 to +76 with respect to desmin transcription start site | CGAGATAACCAGGGCTGAAAGAGGCCCG CCTGGGGGCTGGAGACATGCTTGCTGCC TGCCCTGGCGAAGGATTGGCAGGCTTGC CCGTCACAGGACCCCCGCTGGCTGACTC AGGGGCGCAGGCCTCTTGCGGGGGAGCT GGCCTCCCCGCCCCCACGGCCACGGGCC GCCCTTTCCTGGCAGGACAGCGGGATCTT GCAGCTGTCAGGGGAGGGGAGGCGGGG GCTGATGTCAGGAGGGATACAAATAGTGC CGACGGCTGGGGCCCTGTCTCCCCTCG CCGCATCCACTCTCCGGCCGGCCGCCTG TCCGCCGCCTCCTCCGTGCGCCCGCCAG CCTCGCCCG |
| 7 | Segment of desmin promoter containing SEQ ID NO: 5 fused to SEQ ID NO: 6 | TACCCCCTGCCCCCCACAGCTCCTCTCCT GTGCCTTGTTTCCCAGCCATGCGTTCTCC TCTATAAATACCCGCTCTGGTATTTGGGG TTGGCAGCTGTTGCTGCCAGGGAGATGG TTGGGTTGACATGCGGCTCCTGACAAAAC ACAAACCCTGGTGTGTGTGGGCGTGGG TGGTGTGAGTAGGGGGATGAATCAGGGA GGGGGCGGGGGACCCAGGGGGCAGGAG CCACACAAAGTCTGTGCGGGGGTGGGAG CGCACATAGCAATTGGAAACTGAAAGCTT ATCAGACCCTTTCTGGAAATCAGCCCACT GTTTATAAACTTGAGGCCCCACCCTCGAG CGAGATAACCAGGGCTGAAAGAGGCCCG CCTGGGGGCTGGAGACATGCTTGCTGCC TGCCCTGGCGAAGGATTGGCAGGCTTGC CCGTCACAGGACCCCCGCTGGCTGACTC AGGGGCGCAGGCCTCTTGCGGGGGAGCT GGCCTCCCCGCCCCCACGGCCACGGGCC GCCCTTTCCTGGCAGGACAGCGGGATCTT GCAGCTGTCAGGGGAGGGGAGGCGGGG GCTGATGTCAGGAGGGATACAAATAGTGC CGACGGCTGGGGCCCTGTCTCCCCTCG CCGCATCCACTCTCCGGCCGGCCGCCTG TCCGCCGCCTCCTCCGTGCGCCCGCCAG CCTCGCCCG |
| 8 | Synapsin promoter, including nucleotides −465 to −90 with respect to synapsin transcription start site | AAAATGCCTTCTGAGTTGAATATCAACACT ACAAACCGAGTATCTGCAGAGGGCCCTG CGTATGAGTGCAAGTGGGTTTTAGGACCA GGATGAGGCGGGGTGGGGGTGCCTACCT GACGACCGACCCCGACCCACTGGACAAG CACCCAACCCCCATTCCCCAAATTGCGCA TCCCCTATCAGAGAGGGGGAGGGGAAAC AGGATGCGGCGAGGCGCGTGCGCACTGC CAGCTTCAGCACCGCGGACAGTGCCTTC GCCCCCGCCTGGCGGCGCGCGCCACCG CCGCCTCAGCACTGAAGGCGCGCTGACG TCACTCGCCGGTCCCCCGCAAACTCCCCT TCCCGGCCACCTTGGTCGCGTCCGCGCC GCCGCCG |

In addition to the regulatory elements described above, regulatory elements described herein include those formed by combining the ApoE-HCR element, or a functional portion thereof, to a desmin promoter and/or synapsin promoter, or functional portion thereof. For example, regulatory element useful in conjunction with the compositions and methods described herein include those that contain the 193-nucleotide segment of the ApoE-HCR, set forth in SEQ ID NO: 1, operably linked to a desmin promoter or functional portion thereof. The functional portion of the desmin promoter may be, for example, the nucleic acid spanning nucleotides −984 to −644 with respect to the desmin transcription start site, or the nucleic acid spanning nucleotides −269 to +76 with respect to the desmin transcription start site. In some embodiments, the ApoE-HCR element, or functional portion thereof, is operably linked to a desmin promoter that contains from nucleotide −984 to nucleotide −644 and from nucleotide −269 to nucleotide +76, with respect to the desmin transcription start site, of the human desmin locus. Transcription regulatory elements described herein may also include the synapsin promoter, or a functional portion thereof, in combination with the ApoE-HCR and/or desmin regulatory elements.

Exemplary combinations of transcription regulatory elements are set forth in Table 3, below.

TABLE 3

Combinatorial transcription regulatory elements

| SEQ ID NO. | Description of Transcription Regulatory Element | Nucleic Acid Sequence |
|---|---|---|
| 10 | From 5' to 3':<br>(i) 193-nucleotide segment of ApoE HCR locus fused to<br>(ii) desmin promoter (spanning nucleotides -984 to -644 and nucleotides -269 to +76 with respect to the desmin transcription start site) | CCCCTAAAATGGGCAAACATTGCAAGCAG CAAACAGCAAACACACAGCCCTCCCTGCC TGCTGACCTTGGAGCTGGGGCAGAGGTC AGAGACCTCTCTGGGCCCATGCCACCTCC AACATCCACTCGACCCCTTGGAATTTCGG TGGAGAGGAGCAGAGGTTGTCCTGGCGT GGTTTAGGTAGTGTGAGAGGGTACCCCCT GCCCCCCACAGCTCCTCTCCTGTGCCTTG TTTCCCAGCCATGCGTTCTCCTCTATAAAT ACCCGCTCTGGTATTTGGGGTTGGCAGCT GTTGCTGCCAGGGAGATGGTTGGGTTGA CATGCGGCTCCTGACAAAACACAAACCCC TGGTGTGTGTGGGCGTGGGTGGTGTGAG TAGGGGGATGAATCAGGGAGGGGGCGG GGGACCCAGGGGGCAGGAGCCACACAAA GTCTGTGCGGGGTGGGAGCGCACATAG CAATTGGAAACTGAAAGCTTATCAGACCC TTTCTGGAAATCAGCCCACTGTTTATAAAC TTGAGGCCCCACCCTCGAGCGAGATAAC CAGGGCTGAAAGAGGCCCGCCTGGGGGC TGGAGACATGCTTGCTGCCTGCCCTGGC GAAGGATTGGCAGGCTTGCCCGTCACAG GACCCCCGCTGGCTGACTCAGGGGCGCA GGCCTCTTGCGGGGGAGCTGGCCTCCCC GCCCCCACGGCCACGGGCCGCCCTTTCC TGGCAGGACAGCGGGATCTTGCAGCTGT CAGGGGAGGGGAGGCGGGGGCTGATGT CAGGAGGGATACAAATAGTGCCGACGGC TGGGGGCCCTGTCTCCCCTCGCCGCATC CACTCTCCGGCCGGCCGCCTGTCCGCCG CCTCCTCCGTGCGCCCGCCAGCCTCGCC CG |
| 11 | From 5' to 3':<br>(i) synapsin promoter (spanning nucleotides -465 to -90 with respect to synapsin transcription start site) fused to<br>(ii) 193-nucleotide segment of ApoE HCR locus fused to<br>(iii) desmin promoter (spanning nucleotides -984 to -644 and nucleotides -269 to +76 with respect to the desmin transcription start site) | AAAATGCCTTCTGAGTTGAATATCAACACT ACAAACCGAGTATCTGCAGAGGGCCCTG CGTATGAGTGCAAGTGGGTTTTAGGACCA GGATGAGGCGGGGTGGGGGTGCCTACCT GACGACCGACCCCGACCCACTGGACAAG CACCCAACCCCCATTCCCCAAATTGCGCA TCCCCTATCAGAGAGGGGGAGGGGAAAC AGGATGCGGCGAGGCGCGTGCGCACTGC CAGCTTCAGCACCGCGGACAGTGCCTTC GCCCCCGCCTGGCGGCGCGCGCCACCG CCGCCTCAGCACTGAAGGCGCGCTGACG TCACTCGCCGGTCCCCCGCAAACTCCCCT TCCCGGCCACCTTGGTCGCGTCCGCGCC GCCGCCGCCCCTAAAATGGGCAAACATTG CAAGCAGCAAACAGCAAACACACAGCCCT CCCTGCCTGCTGACCTTGGAGCTGGGGC AGAGGTCAGAGACCTCTCTGGGCCCATG CCACCTCCAACATCCACTCGACCCCTTGG AATTTCGGTGGAGAGGAGCAGAGGTTGTC CTGGCGTGGTTTAGGTAGTGTGAGAGGG TACCCCCTGCCCCCCACAGCTCCTCTCCT GTGCCTTGTTTCCCAGCCATGCGTTCTCC TCTATAAATACCCGCTCTGGTATTTGGGG TTGGCAGCTGTTGCTGCCAGGGAGATGG TTGGGTTGACATGCGGCTCCTGACAAAAC ACAAACCCTGGTGTGTGTGGGCGTGGG TGGTGTGAGTAGGGGGATGAATCAGGGA GGGGGCGGGGGACCCAGGGGGCAGGAG CCACACAAAGTCTGTGCGGGGTGGGAG CGCACATAGCAATTGGAAACTGAAAGCTT ATCAGACCCTTTCTGGAAATCAGCCCACT GTTTATAAACTTGAGGCCCCACCCTCGAG CGAGATAACCAGGGCTGAAAGAGGCCCG CCTGGGGGCTGGAGACATGCTTGCTGCC TGCCCTGGCGAAGGATTGGCAGGCTTGC CCGTCACAGGACCCCCGCTGGCTGACTC AGGGGCGCAGGCCTCTTGCGGGGGAGCT GGCCTCCCCGCCCCCACGGCCACGGGCC GCCCTTTCCTGGCAGGACAGCGGGATCTT |

TABLE 3-continued

Combinatorial transcription regulatory elements

| SEQ ID NO. | Description of Transcription Regulatory Element | Nucleic Acid Sequence |
|---|---|---|
| | | GCAGCTGTCAGGGGAGGGGAGGCGGGG<br>GCTGATGTCAGGAGGGATACAAATAGTGC<br>CGACGGCTGGGGGCCCTGTCTCCCCTCG<br>CCGCATCCACTCTCCGGCCGGCCGCCTG<br>TCCGCCGCCTCCTCCGTGCGCCCGCCAG<br>CCTCGCCCG |
| 12 | From 5' to 3':<br>(i) 50-nucleotide segment of ApoE HCR locus fused to<br>(ii) desmin promoter (spanning nucleotides -984 to -644 and nucleotides -269 to +76 with respect to the desmin transcription start site) | CCCCTAAAATGGGCAAACATTGCAAGCAG<br>CAAACAGCAAACACACAGCCCTACCCCCT<br>GCCCCCCACAGCTCCTCTCCTGTGCCTTG<br>TTTCCCAGCCATGCGTTCTCCTCTATAAAT<br>ACCCGCTCTGGTATTTGGGGTTGGCAGCT<br>GTTGCTGCCAGGGAGATGGTTGGGTTGA<br>CATGCGGCTCCTGACAAAACACAAACCCC<br>TGGTGTGTGTGGGCGTGGGTGGTGTGAG<br>TAGGGGGATGAATCAGGGAGGGGGCGG<br>GGGACCCAGGGGGCAGGAGCCACACAAA<br>GTCTGTCGGGGGTGGGAGCGCACATAG<br>CAATTGGAAACTGAAAGCTTATCAGACCC<br>TTTCTGGAAATCAGCCCACTGTTTATAAAC<br>TTGAGGCCCCACCCTCGAGCGAGATAAC<br>CAGGGCTGAAAGAGGCCCGCCTGGGGGC<br>TGGAGACATGCTTGCTGCCTGCCCTGGC<br>GAAGGATTGGCAGGCTTGCCCGTCACAG<br>GACCCCCGCTGGCTGACTCAGGGGCGCA<br>GGCCTCTTGCGGGGGAGCTGGCCTCCCC<br>GCCCCCACGGCCACGGGCCGCCCTTTCC<br>TGGCAGGACAGCGGGATCTTGCAGCTGT<br>CAGGGGAGGGGAGGCGGGGGCTGATGT<br>CAGGAGGGATACAAATAGTGCCGACGGC<br>TGGGGGCCCTGTCTCCCCTCGCCGCATC<br>CACTCTCCGGCCGGCCGCCTGTCCGCCG<br>CCTCCTCCGTGCGCCCGCCAGCCTCGCC<br>CG |

Additional nucleic acid regulatory elements useful in conjunction with the compositions and methods described herein include nucleic acid molecules that have at least 85% sequence identity (e.g., 86%, 87%, 88%, 89%, 90%, 91%, 92%, 93%, 94%, 95%, 96%, 97%, 98%, 99%, 99.9%, or greater, sequence identity) with respect to the nucleic acid sequences set forth in Table 3.

Methods for the Delivery of Exogenous Nucleic Acids to Target Cells

Transfection Techniques

Techniques that can be used to introduce a transgene, such as a transgene operably linked to a transcription regulatory element described herein, into a target cell are known in the art. For example, electroporation can be used to permeabilize mammalian cells (e.g., human target cells) by the application of an electrostatic potential to the cell of interest. Mammalian cells, such as human cells, subjected to an external electric field in this manner are subsequently predisposed to the uptake of exogenous nucleic acids. Electroporation of mammalian cells is described in detail, e.g., in Chu et al., Nucleic Acids Research 15:1311 (1987), the disclosure of which is incorporated herein by reference. A similar technique, Nucleofection™, utilizes an applied electric field in order to stimulate the uptake of exogenous polynucleotides into the nucleus of a eukaryotic cell. Nucleofection™ and protocols useful for performing this technique are described in detail, e.g., in Distler et al., Experimental Dermatology 14:315 (2005), as well as in US 2010/0317114, the disclosures of each of which are incorporated herein by reference.

Additional techniques useful for the transfection of target cells include the squeeze-poration methodology. This technique induces the rapid mechanical deformation of cells in order to stimulate the uptake of exogenous DNA through membranous pores that form in response to the applied stress. This technology is advantageous in that a vector is not required for delivery of nucleic acids into a cell, such as a human target cell. Squeeze-poration is described in detail, e.g., in Sharei et al., Journal of Visualized Experiments 81: e50980 (2013), the disclosure of which is incorporated herein by reference.

Lipofection represents another technique useful for transfection of target cells. This method involves the loading of nucleic acids into a liposome, which often presents cationic functional groups, such as quaternary or protonated amines, towards the liposome exterior. This promotes electrostatic interactions between the liposome and a cell due to the anionic nature of the cell membrane, which ultimately leads to uptake of the exogenous nucleic acids, for example, by direct fusion of the liposome with the cell membrane or by endocytosis of the complex. Lipofection is described in detail, for example, in U.S. Pat. No. 7,442,386, the disclosure of which is incorporated herein by reference. Similar techniques that exploit ionic interactions with the cell membrane to provoke the uptake of foreign nucleic acids include contacting a cell with a cationic polymer-nucleic acid complex. Exemplary cationic molecules that associate with polynucleotides so as to impart a positive charge favorable for interaction with the cell membrane are activated dendrimers (described, e.g., in Dennig, Topics in Current Chemistry 228:227 (2003), the disclosure of which is incorporated herein by reference) and diethylaminoethyl (DEAE)-dextran, the use of which as a transfection agent is described in detail, for example, in Gulick et al., Current Protocols in Molecular Biology 40:1:9.2:9.2.1 (1997), the disclosure of which is incorporated herein by reference. Magnetic beads are another tool that can be used to transfect target cells in a mild and efficient manner, as this methodology utilizes an applied magnetic field in order to direct the uptake of nucleic acids. This technology is described in detail, for example, in US 2010/0227406, the disclosure of which is incorporated herein by reference.

Another useful tool for inducing the uptake of exogenous nucleic acids by target cells is laserfection, a technique that involves exposing a cell to electromagnetic radiation of a particular wavelength in order to gently permeabilize the cells and allow polynucleotides to penetrate the cell membrane. This technique is described in detail, e.g., in Rhodes et al., Methods in Cell Biology 82:309 (2007), the disclosure of which is incorporated herein by reference.

Microvesicles represent another potential vehicle that can be used to modify the genome of a target cell according to the methods described herein. For example, microvesicles that have been induced by the co-overexpression of the glycoprotein VSV-G with, e.g., a genome-modifying protein, such as a nuclease, can be used to efficiently deliver proteins into a cell that subsequently catalyze the site-specific cleavage of an endogenous polynucleotide sequence so as to prepare the genome of the cell for the covalent incorporation of a polynucleotide of interest, such as a gene or regulatory sequence. The use of such vesicles, also referred to as Gesicles, for the genetic modification of eukaryotic cells is described in detail, e.g., in Quinn et al., Genetic Modification of Target Cells by Direct Delivery of Active Protein [abstract]. In: Methylation changes in early embryonic genes in cancer [abstract], in: Proceedings of the 18th Annual Meeting of the American Society of Gene and Cell Therapy; 2015 May 13, Abstract No. 122.

Incorporation of Target Genes by Gene Editing Techniques

In addition to the above, a variety of tools have been developed that can be used for the incorporation of a gene of interest into a target cell, such as a human cell. One such method that can be used for incorporating polynucleotides encoding target genes into target cells involves the use of transposons. Transposons are polynucleotides that encode transposase enzymes and contain a polynucleotide sequence or gene of interest flanked by 5' and 3' excision sites. Once a transposon has been delivered into a cell, expression of the transposase gene commences and results in active enzymes that cleave the gene of interest from the transposon. This activity is mediated by the site-specific recognition of transposon excision sites by the transposase. In some instances, these excision sites may be terminal repeats or inverted terminal repeats. Once excised from the transposon, the gene of interest can be integrated into the genome of a mammalian cell by transposase-catalyzed cleavage of similar excision sites that exist within the nuclear genome of the cell. This allows the gene of interest to be inserted into the cleaved nuclear DNA at the complementary excision sites, and subsequent covalent ligation of the phosphodiester bonds that join the gene of interest to the DNA of the mammalian cell genome completes the incorporation process. In certain cases, the transposon may be a retrotransposon, such that the gene encoding the target gene is first transcribed to an RNA product and then reverse-transcribed to DNA before incorporation in the mammalian cell genome. Exemplary transposon systems are the piggybac transposon (described in detail in, e.g., WO 2010/085699) and the sleeping beauty transposon (described in detail in, e.g., US 2005/0112764), the disclosures of each of which are incorporated herein by reference as they pertain to transposons for use in gene delivery to a cell of interest.

Another tool for the integration of target genes into the genome of a target cell is the clustered regularly interspaced short palindromic repeats (CRISPR)/Cas system, a system that originally evolved as an adaptive defense mechanism in bacteria and archaea against viral infection. The CRISPR/Cas system includes palindromic repeat sequences within plasmid DNA and an associated Cas9 nuclease. This ensemble of DNA and protein directs site specific DNA cleavage of a target sequence by first incorporating foreign DNA into CRISPR loci. Polynucleotides containing these foreign sequences and the repeat-spacer elements of the CRISPR locus are in turn transcribed in a host cell to create a guide RNA, which can subsequently anneal to a target sequence and localize the Cas9 nuclease to this site. In this manner, highly site-specific cas9-mediated DNA cleavage can be engendered in a foreign polynucleotide because the interaction that brings cas9 within close proximity of the target DNA molecule is governed by RNA:DNA hybridization. As a result, one can design a CRISPR/Cas system to cleave any target DNA molecule of interest. This technique has been exploited in order to edit eukaryotic genomes (Hwang et al., Nature Biotechnology 31:227 (2013)) and can be used as an efficient means of site-specifically editing target cell genomes in order to cleave DNA prior to the incorporation of a gene encoding a target gene. The use of CRISPR/Cas to modulate gene expression has been described in, for example, U.S. Pat. No. 8,697,359, the disclosure of which is incorporated herein by reference as it pertains to the use of the CRISPR/Cas system for genome editing. Alternative methods for site-specifically cleaving genomic DNA prior to the incorporation of a gene of interest in a target cell include the use of zinc finger nucleases (ZFNs) and transcription activator-like effector nucleases (TALENs). Unlike the CRISPR/Cas system, these enzymes do not contain a guiding polynucleotide to localize to a specific target sequence. Target specificity is instead controlled by DNA binding domains within these enzymes. The use of ZFNs and TALENs in genome editing applications is described, e.g., in Urnov et al., Nature Reviews Genetics 11:636 (2010); and in Joung et al., Nature Reviews Molecular Cell Biology 14:49 (2013), the disclosure of each of which are incorporated herein by reference as they pertain to compositions and methods for genome editing.

Additional genome editing techniques that can be used to incorporate polynucleotides encoding target genes into the genome of a target cell include the use of ARCUS™ meganucleases that can be rationally designed so as to site-specifically cleave genomic DNA. The use of these enzymes for the incorporation of genes encoding target genes into the genome of a mammalian cell is advantageous in view of the defined structure-activity relationships that have been established for such enzymes. Single chain meganucleases can be modified at certain amino acid positions in order to create nucleases that selectively cleave DNA at desired locations, enabling the site-specific incorporation of a target gene into the nuclear DNA of a target cell. These single-chain nucleases have been described extensively in, for example, U.S. Pat. Nos. 8,021,867 and 8,445,251, the disclosures of each of which are incorporated herein by reference as they pertain to compositions and methods for genome editing.

Vectors for Delivery of Exogenous Nucleic Acids to Target Cells

Viral Vectors for Nucleic Acid Delivery

Viral genomes provide a rich source of vectors that can be used for the efficient delivery of a gene of interest into the genome of a target cell (e.g., a mammalian cell, such as a human cell). Viral genomes are particularly useful vectors for gene delivery because the polynucleotides contained within such genomes are typically incorporated into the genome of a target cell by generalized or specialized transduction. These processes occur as part of the natural viral replication cycle, and do not require added proteins or reagents in order to induce gene integration. Examples of viral vectors include AAV, retrovirus, adenovirus (e.g., Ad5, Ad26, Ad34, Ad35, and Ad48), parvovirus (e.g., adeno-associated viruses), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses, such as picornavirus and alphavirus, and double stranded DNA viruses including adenovirus, herpesvirus (e.g., Herpes Simplex virus types 1 and 2, Epstein-Barr virus, cytomegalovirus), and poxvirus (e.g., vaccinia, modified vaccinia Ankara (MVA), fowlpox and canarypox). Other viruses useful for delivering polynucleotides encoding antibody light and heavy chains or antibody fragments of the invention include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D-type viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996). Other examples include murine leukemia viruses, murine sarcoma viruses, mouse mammary tumor virus, bovine leukemia virus, feline leukemia virus, feline sarcoma virus, avian leukemia virus, human T-cell leukemia virus, baboon endogenous virus, Gibbon ape leukemia virus, Mason Pfizer monkey virus, simian immunodeficiency virus, simian sarcoma virus, Rous sarcoma virus and lentiviruses. Other examples of vectors are described, for example, in U.S. Pat. No. 5,801,030, the disclosure of which is incorporated herein by reference as it pertains to viral vectors for use in gene therapy.

AAV Vectors for Nucleic Acid Delivery

In some embodiments, nucleic acids of the compositions and methods described herein are incorporated into rAAV vectors and/or virions in order to facilitate their introduction into a cell. rAAV vectors useful in the invention are recombinant nucleic acid constructs that include (1) a transgene to be expressed (e.g., a polynucleotide encoding a GAA protein) and (2) viral nucleic acids that facilitate integration and expression of the heterologous genes. The viral nucleic acids may include those sequences of AAV that are required in cis for replication and packaging (e.g., functional ITRs) of the DNA into a virion. In typical applications, the transgene encodes GAA, which is useful for correcting a GAA-deficiency in patients suffering from lysosomal storage disorders, such as Pompe disease. Such rAAV vectors may also contain marker or reporter genes. Useful rAAV vectors have one or more of the AAV WT genes deleted in whole or in part, but retain functional flanking ITR sequences. The AAV ITRs may be of any serotype (e.g., derived from serotype 2) suitable for a particular application. Methods for using rAAV vectors are described, for example, in Tal et al., J. Biomed. Sci. 7:279-291 (2000), and Monahan and Samulski, Gene Delivery 7:24-30 (2000), the disclosures of each of which are incorporated herein by reference as they pertain to AAV vectors for gene delivery.

The nucleic acids and vectors described herein can be incorporated into a rAAV virion in order to facilitate introduction of the nucleic acid or vector into a cell. The capsid proteins of AAV compose the exterior, non-nucleic acid portion of the virion and are encoded by the AAV cap gene. The cap gene encodes three viral coat proteins, VP1, VP2 and VP3, which are required for virion assembly. The construction of rAAV virions has been described, for example, in U.S. Pat. Nos. 5,173,414; 5,139,941; 5,863,541; 5,869,305; 6,057,152; and 6,376,237; as well as in Rabinowitz et al., J. Virol. 76:791-801 (2002) and Bowles et al., J. Virol. 77:423-432 (2003), the disclosures of each of which are incorporated herein by reference as they pertain to AAV vectors for gene delivery.

rAAV virions useful in conjunction with the compositions and methods described herein include those derived from a variety of AAV serotypes including AAV 1, 2, 3, 4, 5, 6, 7, 8 and 9. For targeting muscle cells, rAAV virions that include at least one serotype 1 capsid protein may be particularly useful. rAAV virions that include at least one serotype 6 capsid protein may also be particularly useful, as serotype 6 capsid proteins are structurally similar to serotype 1 capsid proteins, and thus are expected to also result in high expression of GAA in muscle cells. rAAV serotype 9 has also been found to be an efficient transducer of muscle cells. Construction and use of AAV vectors and AAV proteins of different serotypes are described, for example, in Chao et al., Mol. Ther. 2:619-623 (2000); Davidson et al., Proc. Natl. Acad. Sci. USA 97:3428-3432 (2000); Xiao et al., J. Virol. 72:2224-2232 (1998); Halbert et al., J. Virol. 74:1524-1532 (2000); Halbert et al., J. Virol. 75:6615-6624 (2001); and Auricchio et al., Hum. Molec. Genet. 10:3075-3081 (2001), the disclosures of each of which are incorporated herein by reference as they pertain to AAV vectors for gene delivery.

Also useful in conjunction with the compositions and methods described herein are pseudotyped rAAV vectors. Pseudotyped vectors include AAV vectors of a given serotype (e.g., AAV9) pseudotyped with a capsid gene derived from a serotype other than the given serotype (e.g., AAV1, AAV2, AAV3, AAV4, AAV5, AAV6, AAV7, AAV8, etc.). For example, a representative pseudotyped vector is an AAV8 or AAV9 vector encoding a therapeutic protein pseudotyped with a capsid gene derived from AAV serotype 2. Techniques involving the construction and use of pseudotyped rAAV virions are known in the art and are described, for example, in Duan et al., J. Virol. 75:7662-7671 (2001); Halbert et al., J. Virol. 74:1524-1532 (2000); Zolotukhin et al., Methods, 28:158-167 (2002); and Auricchio et al., Hum. Molec. Genet., 10:3075-3081 (2001).

AAV virions that have mutations within the virion capsid may be used to infect particular cell types more effectively than non-mutated capsid virions. For example, suitable AAV mutants may have ligand insertion mutations for the facilitation of targeting AAV to specific cell types. The construction and characterization of AAV capsid mutants including insertion mutants, alanine screening mutants, and epitope tag mutants is described in Wu et al., J. Virol. 74:8635-45 (2000). Other rAAV virions that can be used in methods of the invention include those capsid hybrids that are generated by molecular breeding of viruses as well as by exon shuffling. See, e.g., Soong et al., Nat. Genet., 25:436-439 (2000) and Kolman and Stemmer, Nat. Biotechnol. 19:423-428 (2001).

Methods of Treatment
Pompe Disease

Pompe disease (also known as glycogen storage disease type II, or GSD II) is caused by deficiency of the lysosomal enzyme GAA. The disease is an inborn error of metabolism in which a GAA deficiency ultimately results in glycogen accumulation in all tissues, especially striated muscle cells. In addition, the effect of glycogen accumulation within the central nervous system and its effect on skeletal muscle function have been documented.

Three clinical forms of this disorder are known: infantile, juvenile, and adult. Infantile Pompe disease has its onset shortly after birth and presents with progressive muscular weakness and cardiac failure. Infantile forms of Pompe are also characterized by a rapid development of cardiomyopathy, and patients often display myopathy and neuropathy leading to death typically in the first year of life. Symptoms in adult and juvenile patients occur later in life, and skeletal muscles and neurons are primarily involved. Patients exhibiting this form of Pompe disease eventually die due to respiratory insufficiency. Patients may exceptionally survive for more than six decades. There is a correlation between the severity of the disease and the residual acid α-glucosidase activity, the activity being 10-20% of normal in late onset and less than 2% in early onset forms of the disease.

Human Acid Alpha-Glucosidase

The amino acid sequence of a wild-type GAA is set forth in SEQ ID NO: 14, below:

```
                                        (SEQ ID NO: 14)
MGVRHPPCSHRLLAVCALVSLATAALLGHILLHDFLLVPRELSGSSPVLE

ETHPAHQQGASRPGPRDAQAHPGRPRAVPTQCDVPPNSRFDCAPDKAITQ

EQCEARGCCYIPAKQGLQGAQMGQPWCFFPPSYPSYKLENLSSSEMGYTA

TLTRTTPTFFPKDILTLRLDVMMETENRLHFTIKDPANRRYEVPLETPHV

HSRAPSPLYSVEFSEEPFGVIVRRQLDGRVLLNTTVAPLFFADQFLQLST

SLPSQYITGLAEHLSPLMLSTSWTRITLWNRDLAPTPGANLYGSHPFYLA

LEDGGSAHGVFLLNSNAMDVVLQPSPALSWRSTGGILDVYIFLGPEPKSV

VQQYLDVVGYPFMPPYWGLGFHLCRWGYSSTAITRQVVENMTRAHFPLDV

QWNDLDYMDSRRDFTFNKDGFRDFPAMVQELHQGGRRYMMIVDPAISSSG

PAGSYRPYDEGLRRGVFITNETGQPLIGKVWPGSTAFPDFTNPTALAWWE

DMVAEFHDQVPFDGMWIDMNEPSNFIRGSEDGCPNNELENPPYVPGVVGG

TLQAATICASSHQFLSTHYNLHNLYGLTEAIASHRALVKARGTRPFVISR

STFAGHGRYAGHWTGDVWSSWEQLASSVPEILQFNLLGVPLVGADVCGFL

GNTSEELCVRWTQLGAFYPFMRNHNSLLSLPQEPYSFSEPAQQAMRKALT

LRYALLPHLYTLFHQAHVAGETVARPLFLEFPKDSSTWTVDHQLLWGEAL

LITPVLQAGKAEVTGYFPLGTWYDLQTVPVEALGSLPPPPAAPREPAIHS

EGQWVTLPAPLDTINVHLRAGYIIPLQGPGLTTTESRQQPMALAVALTKG

GEARGELFWDDGESLEVLERGAYTQVIFLARNNTIVNELVRVTSEGAGLQ

LQKVTVLGVATAPQQVLSNGVPVSNFTYSPDTKVLDICVSLLMGEQFLVS

WC
```

Exemplary genes encoding a GAA polypeptide that may be used in conjunction with the compositions and methods described herein include genes encoding the wild-type GAA protein set forth in SEQ ID NO: 14, as well as functional GAA enzymes having at least 85% identical (e.g., 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 14. Genes encoding a GAA polypeptide that may be used in conjunction with the compositions and methods described herein further include those that have one or more amino acid substitutions, such as those that have one or more conservative amino acid substitutions, with respect to the amino acid sequence set forth in SEQ ID NO: 14. For instance, GAA polypeptides that may be used in conjunction with the compositions and methods described herein include those that have 1, 2, 3, 4, 5, 6, 7, 8, 9, 10, 11, 12, 13, 14, 15, 16, 17, 18, 19, 20, 25, or more, conservative amino acid substitutions with respect to the amino acid sequence of SEQ ID NO: 14.

The transcription regulatory elements described herein can be operably linked to a transgene, such as GAA, that is deficient in lysosomal storage disease patients, such as those suffering from Pompe disease. Constructs containing a lysosomal enzyme under the transcriptional control of a regulatory element described herein can be incorporated into a vector (or other transfection agent described herein) and administered to a patient so as to treat a lysosomal storage disorder. Advantageously, the transcription regulatory elements described herein may promote transcription of the gene encoding a deficient lysosomal enzyme (e.g., GAA) in those cells that are affected by the disease, such as muscle cells and cells of the central nervous system. Further, the regulatory elements described herein convey the additional benefit of reducing or eliminating the immune response that may otherwise accompany the introduction of a gene encoding an enzyme for which a patient is deficient. The advantageous properties of the transcription regulatory elements described herein are reported in further detail in Example 1, below.

Pharmaceutical Composition, Routes of Administration, and Unit Doses

The transcription regulatory elements described herein may be operably linked to a transgene, such as a lysosomal enzyme (e.g., GAA) and incorporated into a vehicle for administration into a patient, such as a human patient suffering from a lysosomal storage disorder (for example, Pompe disease). Pharmaceutical compositions containing vectors, such as viral vectors, that contain the transcription regulatory elements described herein operably linked to a therapeutic transgene can be prepared using methods known in the art. For example, such compositions can be prepared using, e.g., physiologically acceptable carriers, excipients or stabilizers (Remington's Pharmaceutical Sciences 16th edition, Osol, A. Ed. (1980); incorporated herein by reference), and in a desired form, e.g., in the form of lyophilized formulations or aqueous solutions.

Viral vectors, such as AAV vectors and others described herein, containing the transcription regulatory element operably linked to a therapeutic transgene may be administered to a patient (e.g., a human patient) by a variety of routes of administration. The route of administration may vary, for example, with the onset and severity of disease, and may include, e.g., intradermal, transdermal, parenteral, intravenous, intramuscular, intranasal, subcutaneous, percutaneous, intratracheal, intraperitoneal, intraarterial, intravascular, inhalation, perfusion, lavage, and oral administration. Intravascular administration includes delivery into the vasculature of a patient. In some embodiments, the administration is into a vessel considered to be a vein (intravenous), and in some administration, the administration is into a vessel considered to be an artery (intraarterial). Veins include, but are not limited to, the internal jugular vein, a peripheral vein, a coronary vein, a hepatic vein, the portal vein, great saphenous vein, the pulmonary vein, superior vena cava, inferior vena cava, a gastric vein, a splenic vein, inferior mesenteric vein, superior mesenteric vein, cephalic vein, and/or femoral vein. Arteries include, but are not limited to, coronary artery, pulmonary artery, brachial artery, internal carotid artery, aortic arch, femoral artery, peripheral artery, and/or ciliary artery. It is contemplated that delivery may be through or to an arteriole or capillary.

Treatment regimens may vary, and often depend on disease severity and the age, weight, and sex of the patient. Treatment may include administration of vectors (e.g., viral vectors) or other agents described herein as useful for the introduction of a gene of interest into a target cell in various unit doses. Each unit dose will ordinarily contain a predetermined-quantity of the therapeutic composition. The quantity to be administered, and the particular route of administration and formulation, are within the skill of those in the clinical arts. A unit dose need not be administered as a single injection but may comprise continuous infusion over a set period of time. Unit doses of the viral vectors described herein may conveniently be described in terms of plaque forming units (pfu) for a viral construct. Unit doses may range, for example, from $10^3$, $10^4$, $10^5$, $10^6$, $10^7$, $10^8$, $10^9$, $10^{10}$, $10^{11}$, $10^{12}$, to $10^{13}$ pfu and higher. Additionally or alternatively, depending on the kind of virus and the titer attainable, one may deliver 1 to 100, 10 to 50, 100-1,000, or up to about or at least about $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, or $1\times10^{15}$, or higher, infectious viral particles (vp), including all values and ranges there between.

Mixtures of the nucleic acids and viral vectors described herein may be prepared in water suitably mixed with one or more excipients, carriers, or diluents. Dispersions may also be prepared in glycerol, liquid polyethylene glycols, and mixtures thereof and in oils. Under ordinary conditions of storage and use, these preparations may contain a preservative to prevent the growth of microorganisms. The pharmaceutical forms suitable for injectable use include sterile aqueous solutions or dispersions and sterile powders for the extemporaneous preparation of sterile injectable solutions or dispersions (described in U.S. Pat. No. 5,466,468, the disclosure of which is incorporated herein by reference). In any case the formulation may be sterile and may be fluid to the extent that easy syringability exists. Formulations may be stable under the conditions of manufacture and storage and may be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For example, a solution containing a pharmaceutical composition described herein may be suitably buffered, if necessary, and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject. Moreover, for human administration, preparations may meet sterility, pyrogenicity, general safety, and purity standards as required by FDA Office of Biologics standards.

EXAMPLES

The following examples are put forth so as to provide those of ordinary skill in the art with a description of how the compositions and methods described herein may be used, made, and evaluated, and are intended to be purely exemplary of the invention and are not intended to limit the scope of what the inventors regard as their invention.

Example 1. Establishing Optimal Tissue Expression for Acid Alpha-Glucosidase Gene Delivery in Pompe Disease Patients Objective Several adeno-associated virus (AAV) vectors were designed to target expression in distinct tissues (e.g., muscle and liver) across a range of doses in a mouse model of Pompe. Outcomes were compared following systemic administration in a Pompe mouse model for six adeno-associated virus (AAV) vectors designed to direct expression of the human acid alpha-glucosidase gene (hGAA) to distinct tissues and/or combinations of tissues across a range of doses. Vectors were selected with the optimal multi-tissue expression profile for translation to clinical trials of systemically administered AAV-GAA for treatment of Pompe disease.

In this study, vector dose and target tissue expression profiles were examined to determine how they impacted a variety of endpoints in this model that are relevant to Pompe disease in patients, including respiratory, cardiac, and skeletal muscle function, and GAA activity and glycogen accumulation in tissues. The findings described herein support the clinical translation of an optimized hGAA vector for AAV gene therapy.

Materials and Methods

Vectors and Vector Production

Vector 2 (AAV9-Des-hGAAco), Vector 3 (AAV8-LDes-hGAAco), Vector 4 (AAV8-LNDes-hGAAco), Vector 5 (AAV8-LDes2-hGAAco), and Vector 6 (AAV8-Des3-hGAAco) were cloned through standard molecular biology techniques and manufactured in a scaled production method based on 2-plasmid transient transfection into mammalian cells. Genome titers for each vector were determined through ddPCR. The candidate vectors are summarized below in Table 4. A schematic of the general organization of the inverted terminal repeat (ITR) region of the constructs is shown in FIG. 1.

TABLE 4

Candidate vectors

| Vector | Description | Nucleic Acid Sequence of Transcription Regulatory Element | Serotype | Promoter Element | Vector dosing (vg/kg)* |
|---|---|---|---|---|---|
| 1 | AAV8-LP1c-hGAAco | SEQ ID NO: 9 | AAV8 | Liver-directed promoter | Minimum dose $(3 \times 10^{12}$ vg/kg); Low dose $(1 \times 10^{13}$ vg/kg) |
| 2 | AAV9-Des-hGAAco | SEQ ID NO: 7 | AAV9 | Desmin promoter | Low dose $(1 \times 10^{13}$ vg/kg); High dose $(3 \times 10^{13}$ vg/kg) |
| 3 | AAV8-LDes-hGAAco | SEQ ID NO: 10 | AAV8 | Desmin/liver putative hybrid promoter | Low dose $(1 \times 10^{13}$ vg/kg); High dose $(3 \times 10^{13}$ vg/kg) |
| 4 | AAV8-LNDes-hGAAco | SEQ ID NO: 11 | AAV8 | Desmin/liver/CNS putative hybrid promoter | Low dose $(1 \times 10^{13}$ vg/kg); High dose $(3 \times 10^{13}$ vg/kg) |
| 5 | AAV8-LDes2-hGAAco | SEQ ID NO: 12 | AAV8 | Desmin/liver putative hybrid promoter | Low dose $(1 \times 10^{13}$ vg/kg); High dose $(3 \times 10^{13}$ vg/kg) |
| 6 | AAV8-Des3-hGAAco | SEQ ID NO: 7 | AAV8 | Desmin promoter | Low dose $(1 \times 10^{13}$ vg/kg); High dose $(3 \times 10^{13}$ vg/kg) |

*To normalize for strong AAV8 liver tropism and expression, Vector 1 was dosed 3-fold lower than Vectors 2-6

Transcription Regulatory Elements

The nucleic acid sequence of the transcription regulatory element operably linked to the GAA transgene in Vector No. 1 contains, from 5'-to-3', a 193-nucleotide segment of the ApoE-HCR (set forth in SEQ ID NO: 1), operably linked to a human alpha-1 anti-trypsin promoter (set forth in SEQ ID NO: 13, below). The nucleic acid sequence of the combined ApoE-HCR/human alpha-1 anti-trypsin regulatory element used in this construct is set forth in SEQ ID NO: 9.

```
                                          (SEQ ID NO: 9)
CCCCTAAAATGGGCAAACATTGCAAGCAGCAAACAGCAAACACACAGCCC

TCCCTGCCTGCTGACCTTGGAGCTGGGGCAGAGGTCAGAGACCTCTCTGG

GCCCATGCCACCTCCAACATCCACTCGACCCCTTGGAATTTCGGTGGAGA

GGAGCAGAGGTTGTCCTGGCGTGGTTTAGGTAGTGTGAGAGGGGAATGAC

TCCTTTCGGTAAGTGCAGTGGAAGCTGTACACTGCCCAGGCAAAGCGTCC

GGGCAGCGTAGGCGGGCGACTCAGATCCCAGCCAGTGcACTTAGCCCCTG

TTTGCTCCTCCGATAACTGGGGTGACCTTGGTTAATATTCACCAGCAGCC

TCCCCCGTTGCCCCTCTGGATCCACTGCTTAAATACGGACGAGGACAGGG

CCCTGTCTCCTCAGCTTCAGGCACCACCACTGACCTGGGACAGTGAATC (SEQ ID NO: 13)
GAATGACTCCTTTCGGTAAGTGCAGTGGAAGCTGTACACTGCCCAGGCAA

AGCGTCCGGGCAGCGTAGGCGGGCGACTCAGATCCCAGCCAGTGcACTTA

GCCCCTGTTTGCTCCTCCGATAACTGGGGTGACCTTGGTTAATATTCACC
```

-continued
```
AGCAGCCTCCCCCGTTGCCCCTCTGGATCCACTGCTTAAATACGGACGAG

GACAGGGCCCTGTCTCCTCAGCTTCAGGCACCACCACTGACCTGGGACAG

TGAATC
```

The nucleic acid sequence of the transcription regulatory element operably linked to the GAA transgene in Vector No. 2 is a shortened desmin promoter. This shortened desmin promoter contains a 5' region having the nucleic acid sequence of SEQ ID NO: 5 (containing nucleotides −984 to −644 with respect to the desmin transcription start site) fused to a 3' region having the nucleic acid sequence of SEQ ID NO: 6 (containing nucleotides −269 to +70 with respect to the desmin transcription start site). The nucleic acid sequence of the transcription regulatory element used in this construct is set forth in SEQ ID NO: 7.

The nucleic acid sequence of the transcription regulatory element operably linked to the GAA transgene in Vector No. 3 contains, from 5'-to-3', a 193-nucleotide segment of the ApoE-HCR (set forth in SEQ ID NO: 1), operably linked to a shortened desmin promoter. This shortened desmin promoter contains a 5' region having the nucleic acid sequence of SEQ ID NO: 5 (containing nucleotides −984 to −644 with respect to the desmin transcription start site) fused to a 3' region having the nucleic acid sequence of SEQ ID NO: 6 (containing nucleotides −269 to +70 with respect to the desmin transcription start site). The nucleic acid sequence of the combined desmin promoter used in this construct is set forth in SEQ ID NO: 7. The nucleic acid sequence of the combined ApoE-HCR/desmin transcription regulatory element used in this construct is set forth in SEQ ID NO: 10.

The nucleic acid sequence of the transcription regulatory element operably linked to the GAA transgene in Vector No. 4 contains, from 5'-to-3', a synapsin promoter, operably linked to a 193-nucleotide segment of the ApoE-HCR, operably linked to a shortened desmin promoter. The nucleic acid sequence of the synapsin promoter used in this construct is set forth in SEQ ID NO: 8 (containing nucleotides −465 to −90 with respect to the synapsin transcription start site). The nucleic acid sequence of the segment of the ApoE-HCR region used in this construct is set forth in SEQ ID NO: 1. The shortened desmin promoter used in this construct contains a 5' region having the nucleic acid sequence of SEQ ID NO: 5 (containing nucleotides −984 to −644 with respect to the desmin transcription start site) fused to a 3' region having the nucleic acid sequence of SEQ ID NO: 6 (containing nucleotides −269 to +70 with respect to the desmin transcription start site). The nucleic acid sequence of the combined desmin promoter used in this construct is set forth in SEQ ID NO: 7. The nucleic acid sequence of the combined synapsin/ApoE-HCR/desmin transcription regulatory element used in this construct is set forth in SEQ ID NO: 11.

The nucleic acid sequence of the transcription regulatory element operably linked to the GAA transgene in Vector No. 5 contains, from 5'-to-3', a 50-nucleotide segment of the ApoE-HCR (set forth in SEQ ID NO: 4), operably linked to a shortened desmin promoter. This shortened desmin promoter contains a 5' region having the nucleic acid sequence of SEQ ID NO: 5 (containing nucleotides −984 to −644 with respect to the desmin transcription start site) fused to a 3' region having the nucleic acid sequence of SEQ ID NO: 6 (containing nucleotides −269 to +70 with respect to the desmin transcription start site). The nucleic acid sequence of the combined desmin promoter used in this construct is set forth in SEQ ID NO: 7. The nucleic acid sequence of the combined ApoE-HCR/desmin transcription regulatory element used in this construct is set forth in SEQ ID NO: 12.

The nucleic acid sequence of the transcription regulatory element operably linked to the GAA transgene in Vector No. 6 is a shortened desmin promoter. This shortened desmin promoter contains a 5' region having the nucleic acid sequence of SEQ ID NO: 5 (containing nucleotides −984 to −644 with respect to the desmin transcription start site) fused to a 3' region having the nucleic acid sequence of SEQ ID NO: 6 (containing nucleotides −269 to +70 with respect to the desmin transcription start site). The nucleic acid sequence of the transcription regulatory element used in this construct is set forth in SEQ ID NO: 7.

In Vivo Studies

All animal procedures were approved by the Institutional Animal Care and Use Committee of Jackson Laboratories, Bar Harbor, ME, and performed at Jackson Laboratories, Bar Harbor, ME. B6.129-Gaaw$^{wt}$ mice and B6.129-Gaa$^{rm1Rabn}$ homozygous mutant mice were obtained from Jackson Laboratories. AAV lots were prepared for injection by dilution in vehicle, and doses were administered through a single intravenous administration of vector or vehicle, following weighing of mice, at $3\times10^{12}$ vg/kg, $1\times10^{13}$ vg/kg, $3\times10^{13}$ vg/kg, or $1\times10^{14}$ vg/kg, as indicated. Clinical observations and mortality observations were conducted daily from administration to the end of the study. At four or twelve weeks post dosing, mice were sacrificed and necropsied. Harvested tissues were processed and sent to third party contract research organizations for subsequent analysis.

GAA Activity

Alpha-glucosidase (GAA) activity was assessed in mouse tissue (e.g., liver, heart, brain, and spine) and serum. Serum or tissue homogenate was incubated with the fluorogenic substrate 4-Methylumbelliferyl α-D-glucopyranoside (4-MUG), which is hydrolyzed by GAA to produce the hydrolysis product 4-Methylumbelliferone (4-MU). 4-MU was detected with a fluorescence plate reader, and enzyme activity in the sample was quantitated using a 4-MU standard curve.

Anti-GAA Antibody Analysis

Maxisorp 96-well plates (Thermo Fisher Scientific) were coated with recombinant hGAA protein (R&D Systems). After blocking, plasma samples diluted at 1:200 were added to plates and incubated for 1 hr at 37° C. Anti-mouse secondary antibodies conjugated to HRP were used for detection. Then, fluorogenic substrate was added to the wells and light intensity was assessed on a plate reader.

RNA-Seq Analysis

Total RNA was isolated from tissues and sequencing libraries were prepared using the standard Illumina strand specific protocol with polyA selection. Libraries were indexed per sample, pooled by tissue type, and sequenced on the Illumina HiSeq across 4 lanes (2×150 bp reads). Adapter sequences were first trimmed from FASTQ files using Skewer, then transcript abundance including hGAA were quantified from the trimmed FASTQ files using Salmon (accounting for GC bias and strand information), and lastly transcript counts were normalized for library size using the DESeq2 package from Bioconductor.

Pathology Assessments

Isopentane-frozen tissue was sectioned and stained with H&E and PAS according to standard procedures. Sections were then analyzed by a trained pathologist in a blinded manner, and assessed a score according to the following rubric (also see Table 5): 1. Normal; 2. Large and small glycogen aggregates seen in 10-49% of fibers; 3. Large and small glycogen aggregates seen in 50-90% of fibers; 4. Small glycogen aggregates in >90% of fibers, with large glycogen aggregates only in rare fibers; 5. Small glycogen aggregates in >90% of fibers, with large glycogen aggregates in >30% of fibers.

Results

Hybrid Promoters Tune GAA Expression Balance in Liver and Muscle

Figure 2:
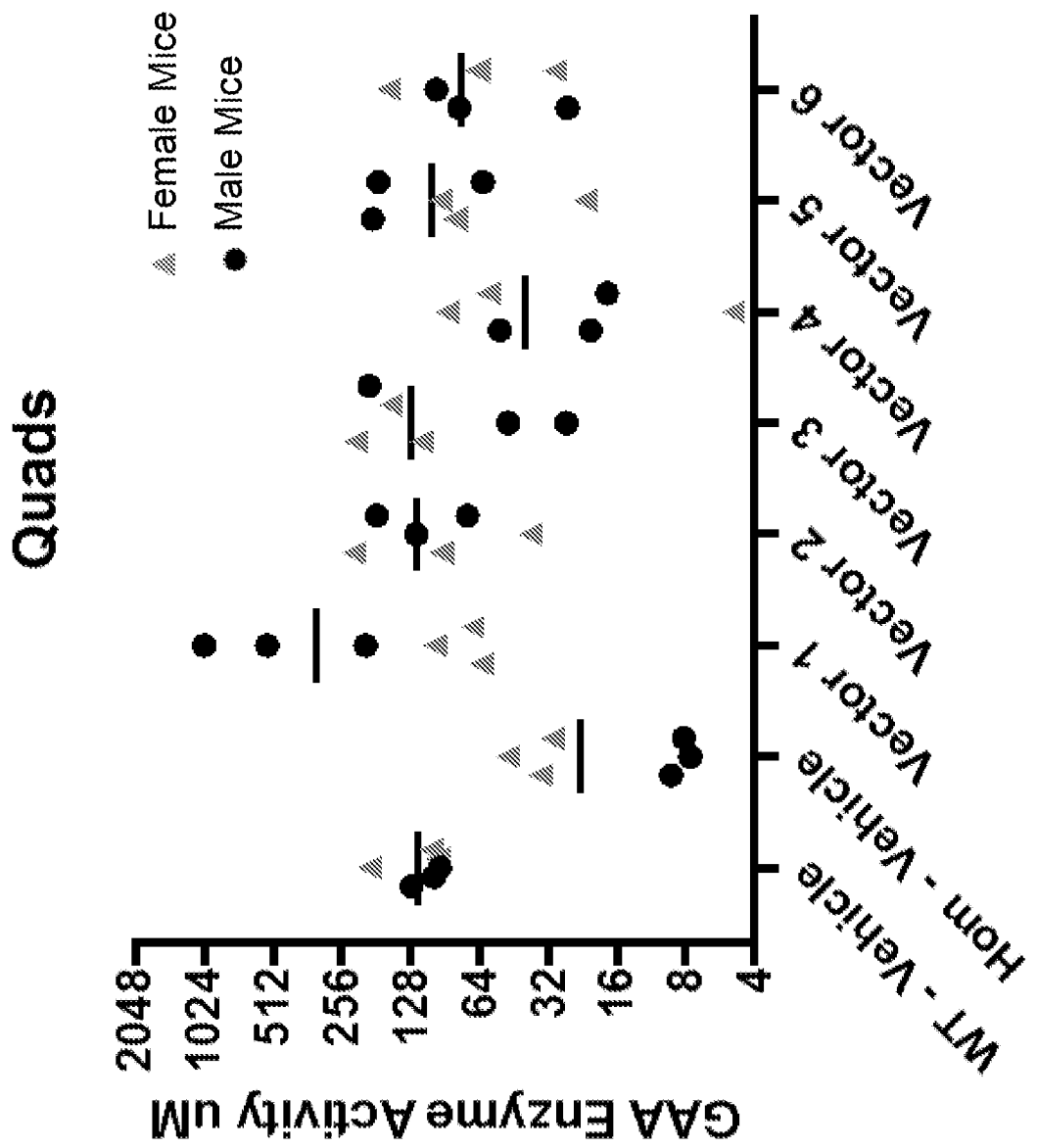
FIG. 2 is a graph showing GAA activity as assessed one month post-dosing in quadriceps tissue from male (black dots) and female mice (grey triangles) for control- and vector-treated mice dosed at $1\times10^{13}$ vg/kg.
Figure 3:
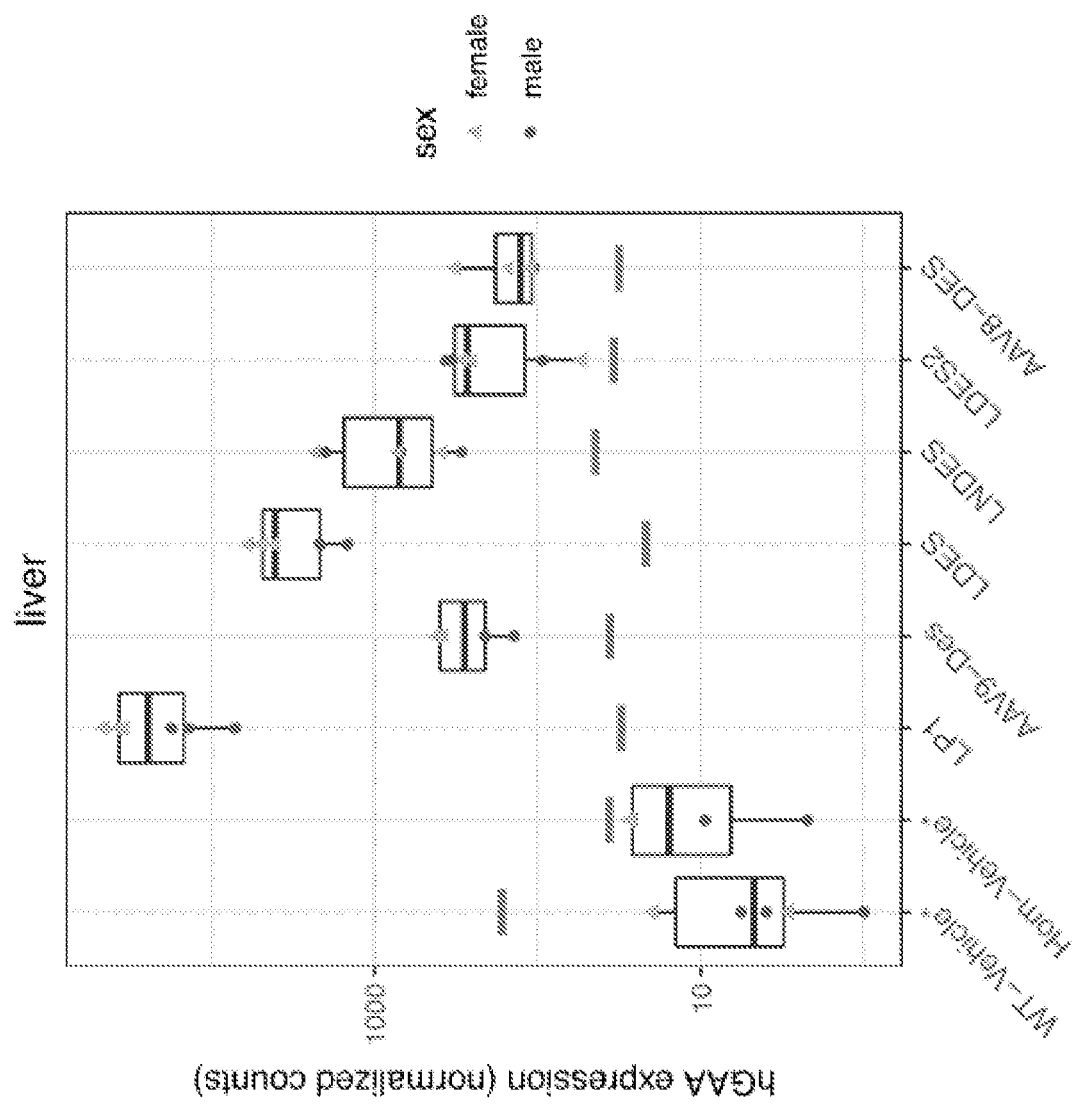
FIG. 3 is a graph showing hGAA transcripts as measured in liver tissue from male (dots) and female mice (triangles) for control- and vector-treated mice dosed at $1\times10^{13}$ vg/kg by RNA-seq analysis. Median expression levels of endogenous murine GAA are indicated by the horizontal lines.
Figure 4:
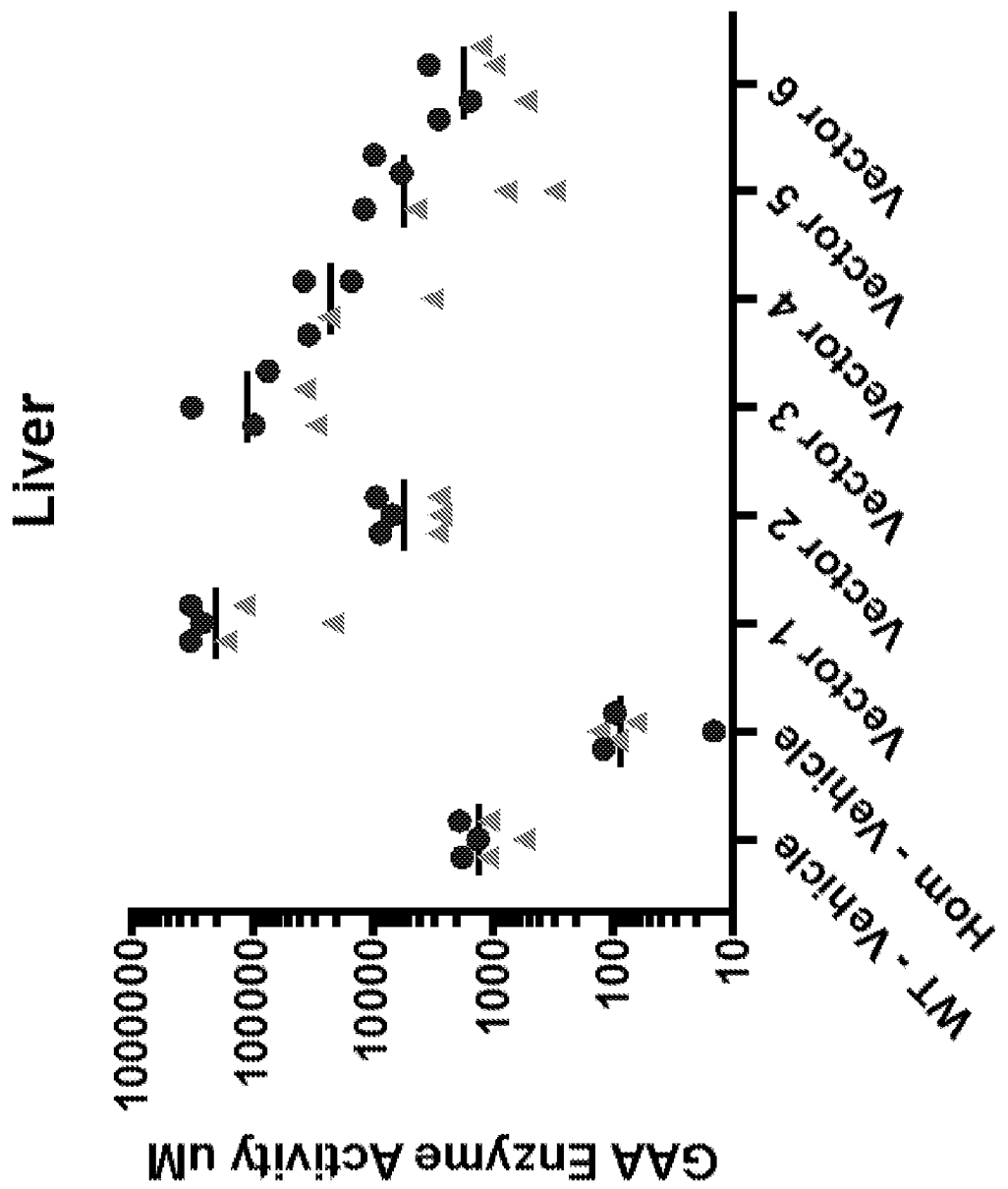
FIG. 4 is a graph showing GAA activity as assessed one month post-dosing in liver tissue from male (black dots) and female mice (grey triangles) for control- and vector-treated mice dosed at $1\times10^{13}$ vg/kg.

GAA activity was assessed in muscle and liver tissue. To determine GAA activity in muscles, GAA activity was assessed one month post-dosing (see materials and methods) in quadriceps tissue from male (black dots) and female mice (grey triangles) for control- and vector-treated mice dosed at $1\times10^{13}$ vg/kg (FIG. 2). To determine GAA activity in liver tissue, GAA activity was assessed one month post-dosing in liver tissue from male (black dots) and female mice (grey triangles) for control- and vector-treated mice dosed at $1\times10^{13}$ vg/kg (FIG. 4). Additionally, hGAA transcripts were measured in liver tissue from male (dots) and female mice (triangles) for control- and vector-treated mice dosed at $1\times10^{13}$ vg/kg by RNA-seq analysis (FIG. 3). Median expression levels of endogenous murine GAA are indicated by the horizontal lines.

These results show that hybrid promoter constructs were expressed in liver and muscle. GAA activity was preserved in quadriceps with muscle-directed hybrid promoter constructs. Consistent with engineered liver-enhanced promoter design, Vector 1 and hybrid Vectors 3 and 4 exhibited the highest levels of expression and activity in liver.

Figure 5B:
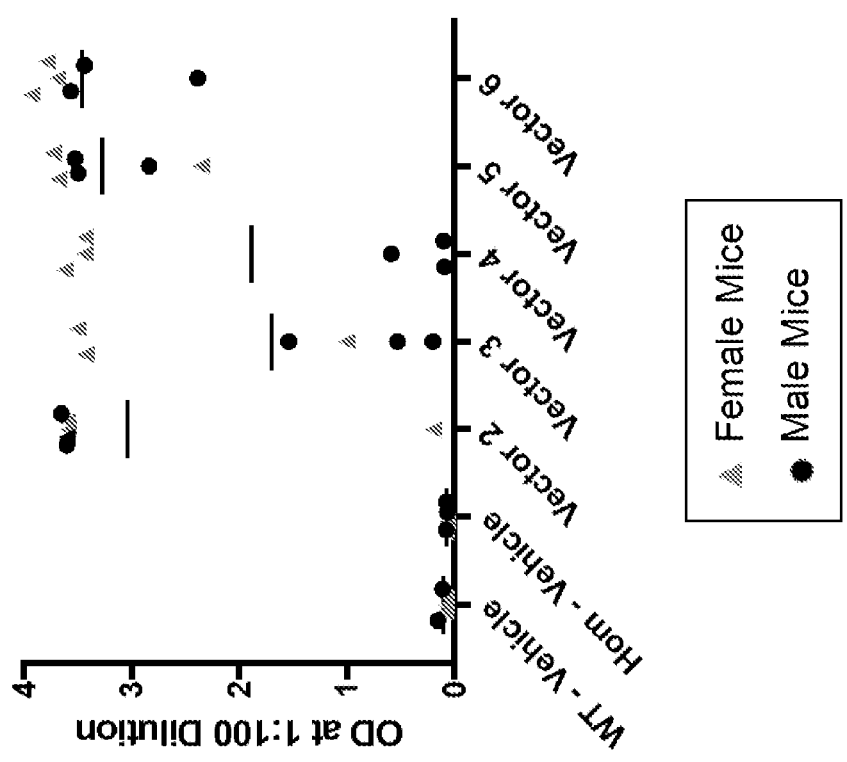
FIGS. 5A and 5B are graphs showing anti-GAA antibody levels as assessed one month post-dosing in serum from male (dots) and female mice (triangles) for control- and vector-treated mice dosed at $1\times10^{13}$ vg/kg (FIG. 5A) or $3\times10^{13}$ vg/kg (FIG. 5B).
Figure 5A:
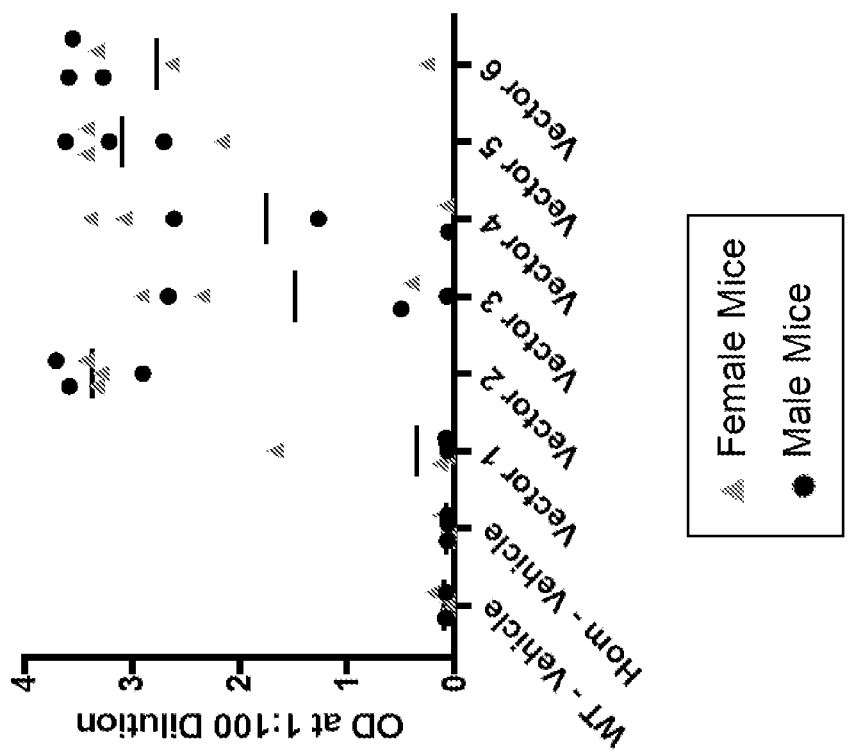
Figure 6B:
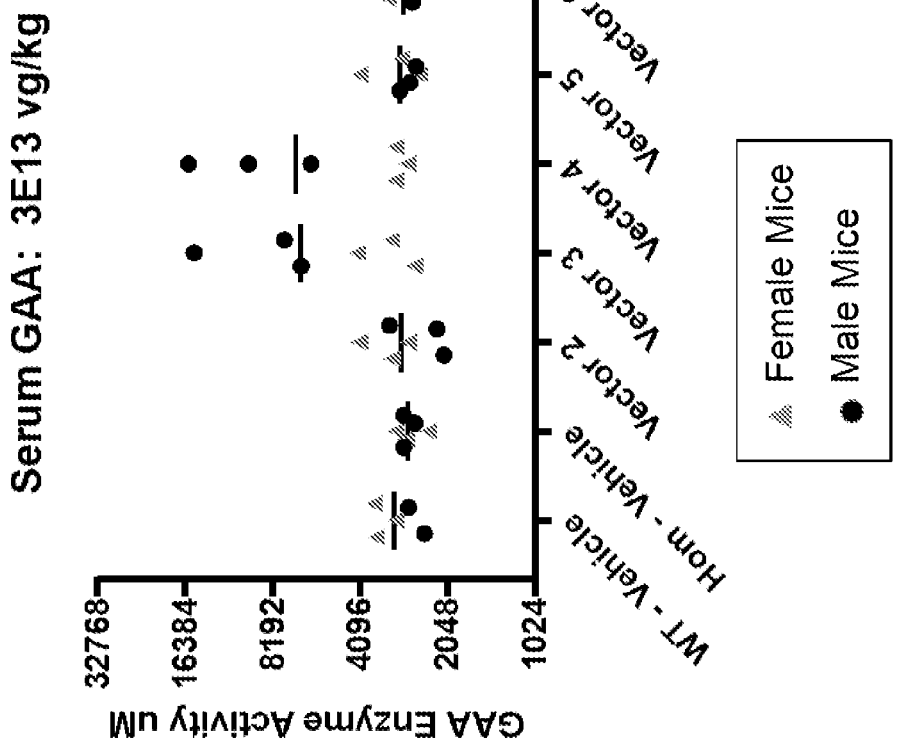
FIGS. 6A and 6B are graphs showing GAA activity as assessed one month post-dosing in serum from male (dots) and female mice (triangles) for control- and vector-treated mice dosed at $1\times10^{13}$ vg/kg (FIG. 6A) or $3\times10^{13}$ vg/kg (FIG. 6B).
Figure 6A:
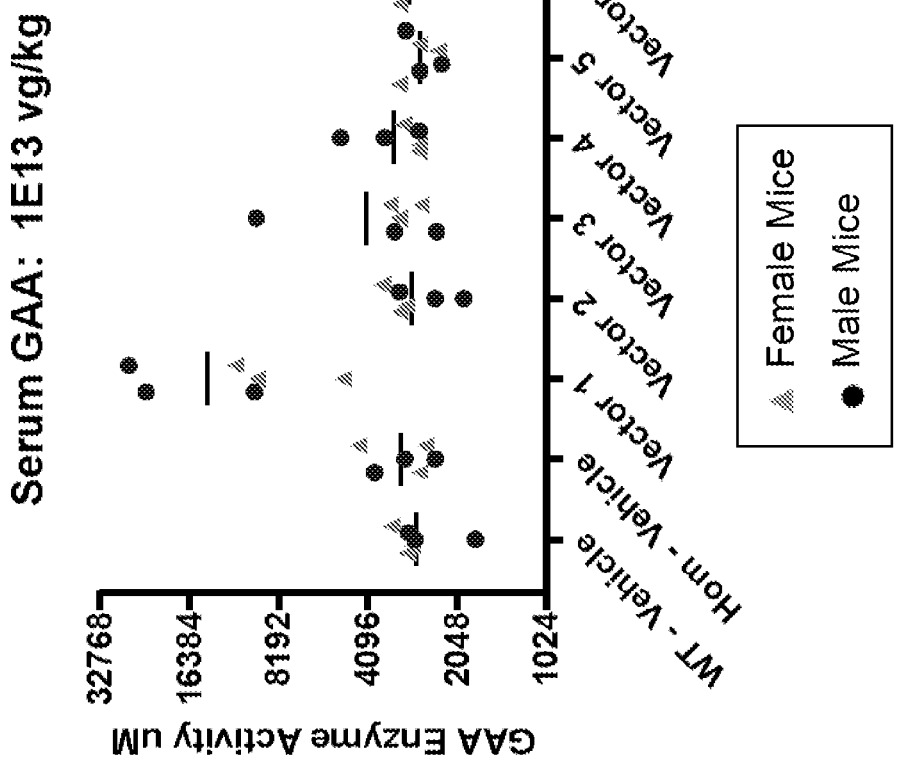

The impact of liver expression on antibody reactivity to hGAA was also evaluated. Anti-GAA antibody levels were assessed one month post-dosing in serum from male (black dots) and female mice (grey triangles) for control- and vector-treated mice dosed at $1\times10^{13}$ vg/kg (FIG. 5A) or $3\times10^{13}$ vg/kg (FIG. 5B). Further, GAA activity was assessed one month post-dosing in serum from male (black dots) and female mice (grey triangles) for control- and vector-treated mice dosed at $1\times10^{13}$ vg/kg (FIG. 6A) or $3\times10^{13}$ vg/kg (FIG. 6B).

Elevated liver expression yields reduced antibody reactivity to hGAA. Reduced antibody reactivity to hGAA yielded elevated serum GAA in Vectors 1, 3, and 4. In summary, elevated liver activity of promoter yielded reduced anti-GAA immunogenicity in a dose-dependent manner, and elevated levels of GAA activity in serum.

Figure 7B:
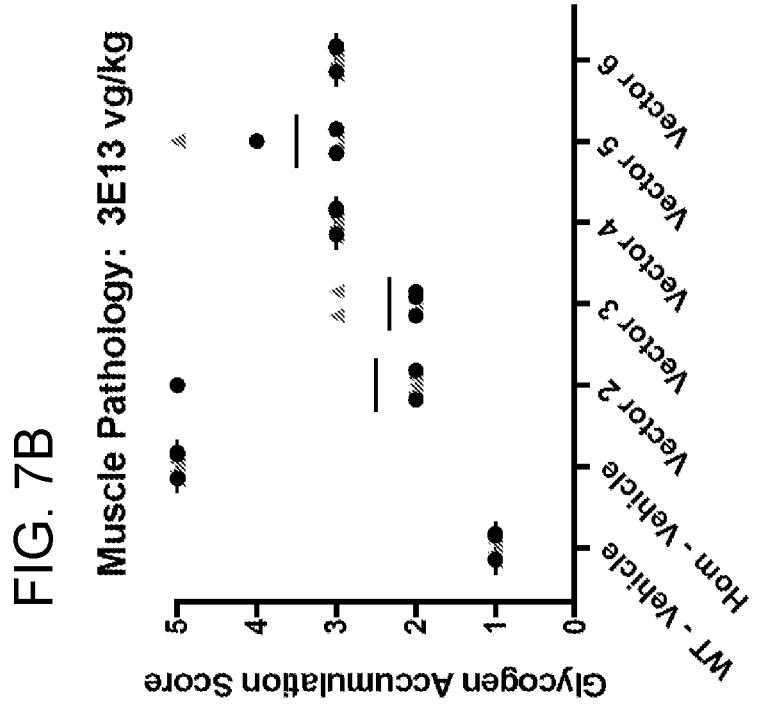
FIGS. 7A and 7B are graphs showing pathology scores (reported in Table 5) in sectioned quadriceps tissue as assessed one month post-dosing from male (dots) and female mice (triangles) for control- and vector-treated mice dosed at $1\times10^{13}$ vg/kg (FIG. 7A) or $3\times10^{13}$ vg/kg (FIG. 7B).
Figure 7A:
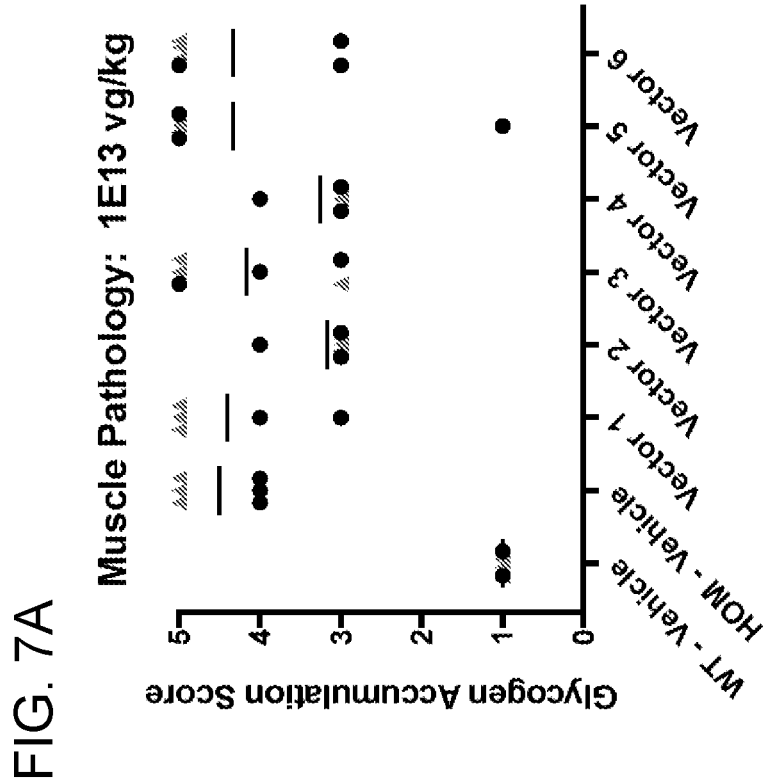

Improved Pathology in Quadriceps from Hybrid Promoter Relative to Liver-Only Promoter Vector Muscle pathology is classically difficult to correct in humans by enzyme replacement therapy. To determine the impact of each vector in improving muscle pathology, pathology scores (Table 5) in sectioned quadriceps tissue were assessed from male (black dots) and female mice (grey triangles) for control- and vector-treated mice dosed at $1\times10^{13}$ vg/kg (FIG. 7A) or $3\times10^{13}$ vg/kg (FIG. 7B).

Figure 8:
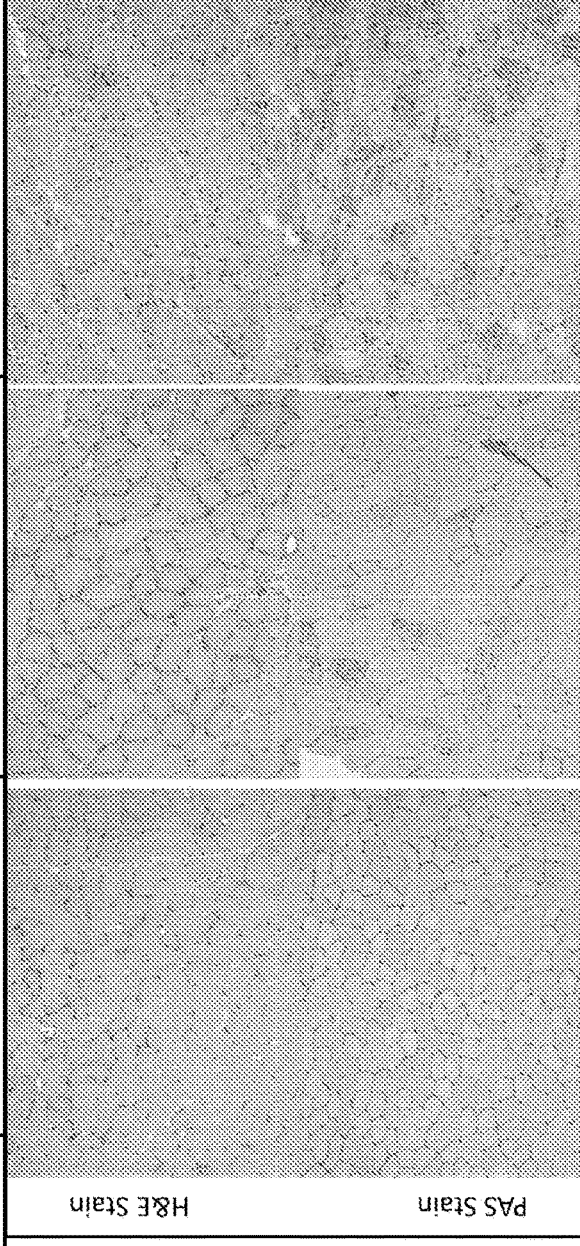
FIG. 8 shows images from H&E and PAS stained sections from representative mice and shows corresponding measures indicating elevated GAA activity, reduced glycogen levels, and muscle pathology repair in mice dosed with vector containing hGAA transgene directed by hybrid promoter and liver-directed promoter. Representative control- and vector-treated mice dosed at $3\times10^{13}$ vg/kg were analyzed for GAA activity in serum and quadriceps, and for glycogen accumulation in quadriceps. A glycogen accumulation score was assessed from tissue sections from isopentane-frozen quadriceps sectioned and stained with H&E and PAS according to standard procedures.

GAA activity, glycogen levels, and muscle pathology repair were assessed in mice dosed with a vector containing hGAA transgene directed by hybrid promoter. Representative control- and vector-treated mice dosed at $3\times10^{13}$ vg/kg were analyzed for GAA activity in serum and quadriceps, and for glycogen accumulation in quadriceps, values for which are reported in FIG. 8. A glycogen accumulation score was assessed from tissue sections from isopentane-frozen quadriceps sectioned and stained with H&E and PAS according to standard procedures, and the values are reported in FIG. 8. Images from H&E and PAS stained sections from representative mice are also shown in FIG. 8.

Muscle expression was required for improved muscle pathology in vivo. Mice dosed with hybrid promoters achieved improved pathology scores in muscle in a GAA mouse model. Several vectors yielded improved pathology scores in male and female mice at $3\times10^{13}$ vg/kg dose.

TABLE 5

Pathology scores

Score Pathology (Lawlor Scoring Rubric)

Figure 9:
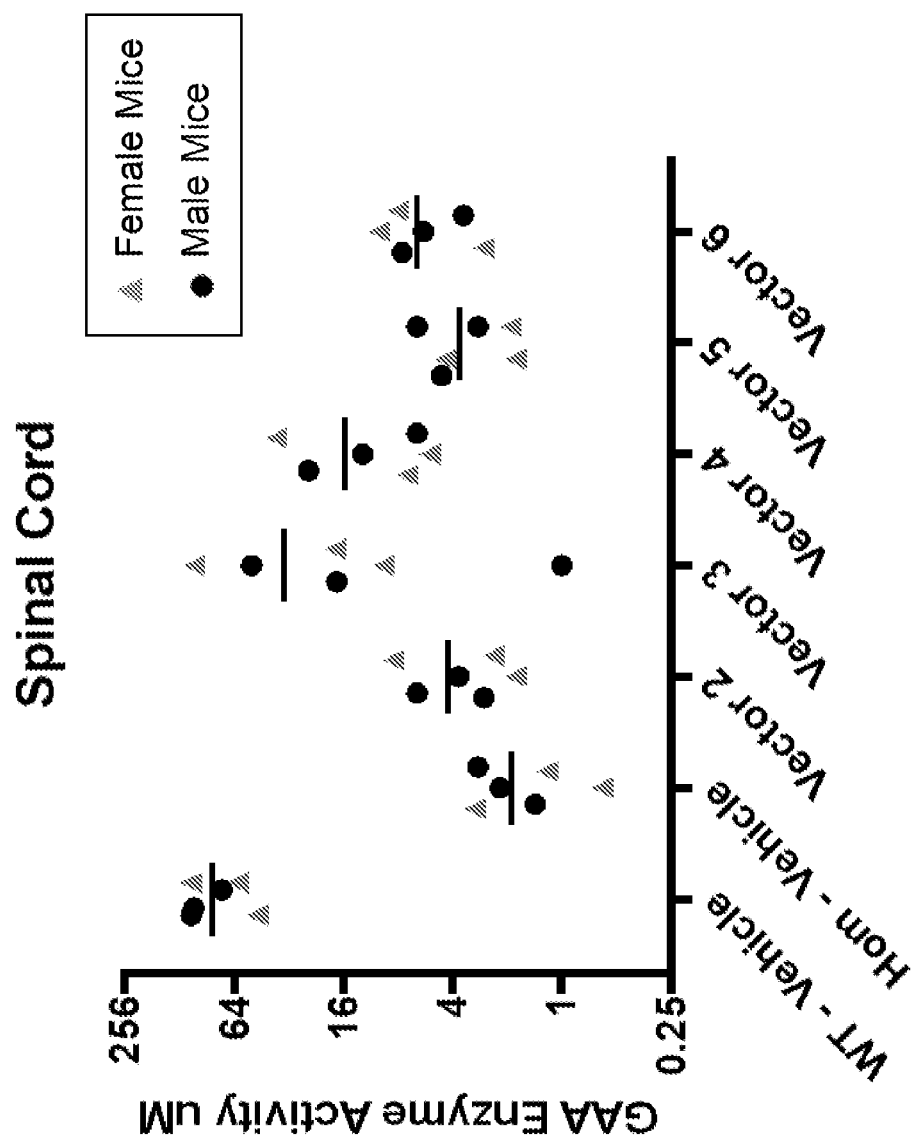
FIG. 9 is a graph showing GAA activity as assessed one month post-dosing in spinal cord from male (black dots) and female mice (grey triangles) for control- and vector-treated mice dosed at $3\times10^{13}$ vg/kg.
Figure 10:
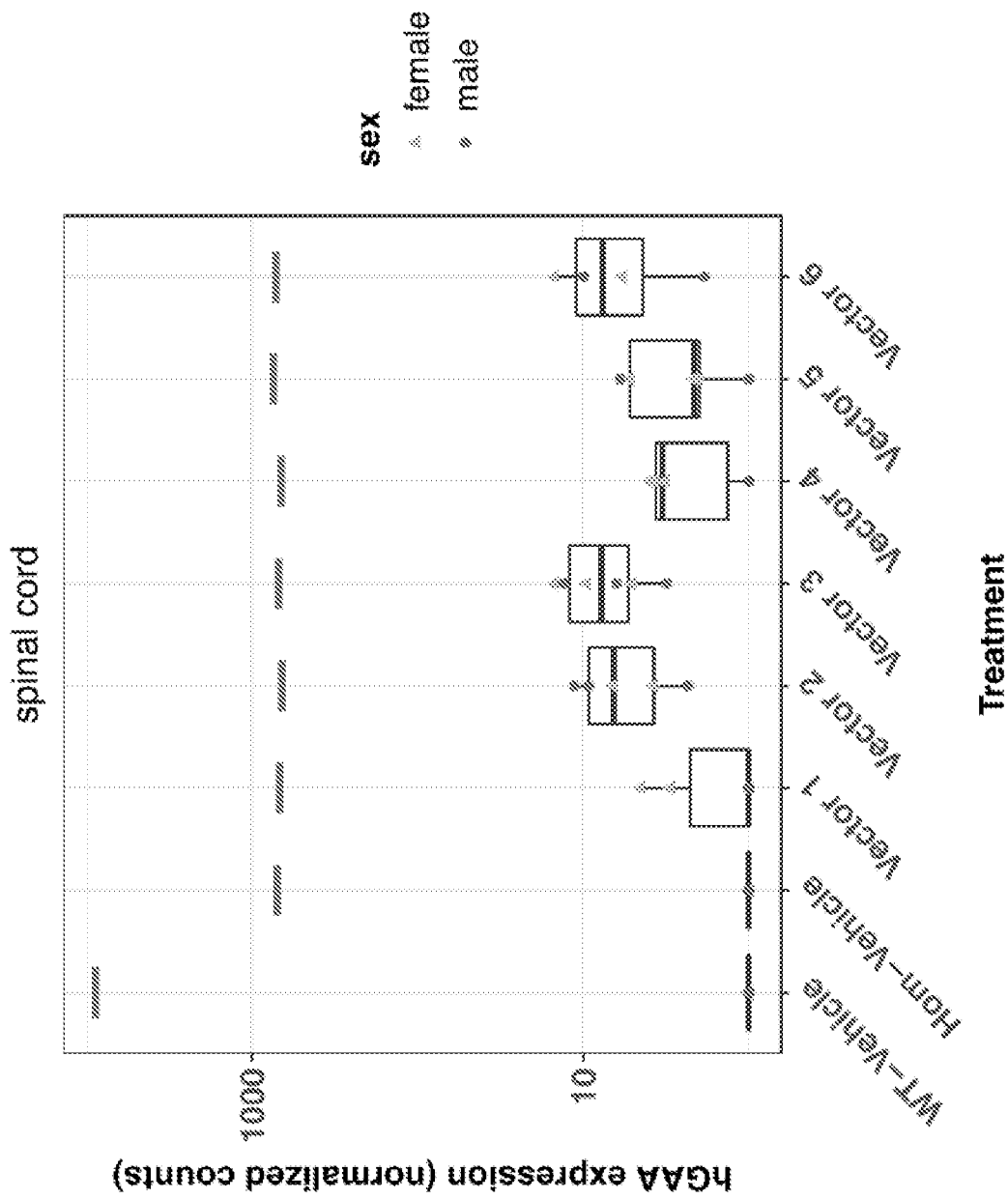
FIG. 10 is a graph showing quantification of hGAA transcripts measured in spinal cord tissue from male (dots) and female mice (triangles) for control- and vector-treated mice dosed at 1×10¹³ vg/kg by RNA-seq analysis. Median expression levels of endogenous murine GAA are indicated by the horizontal lines.
Figure 11:
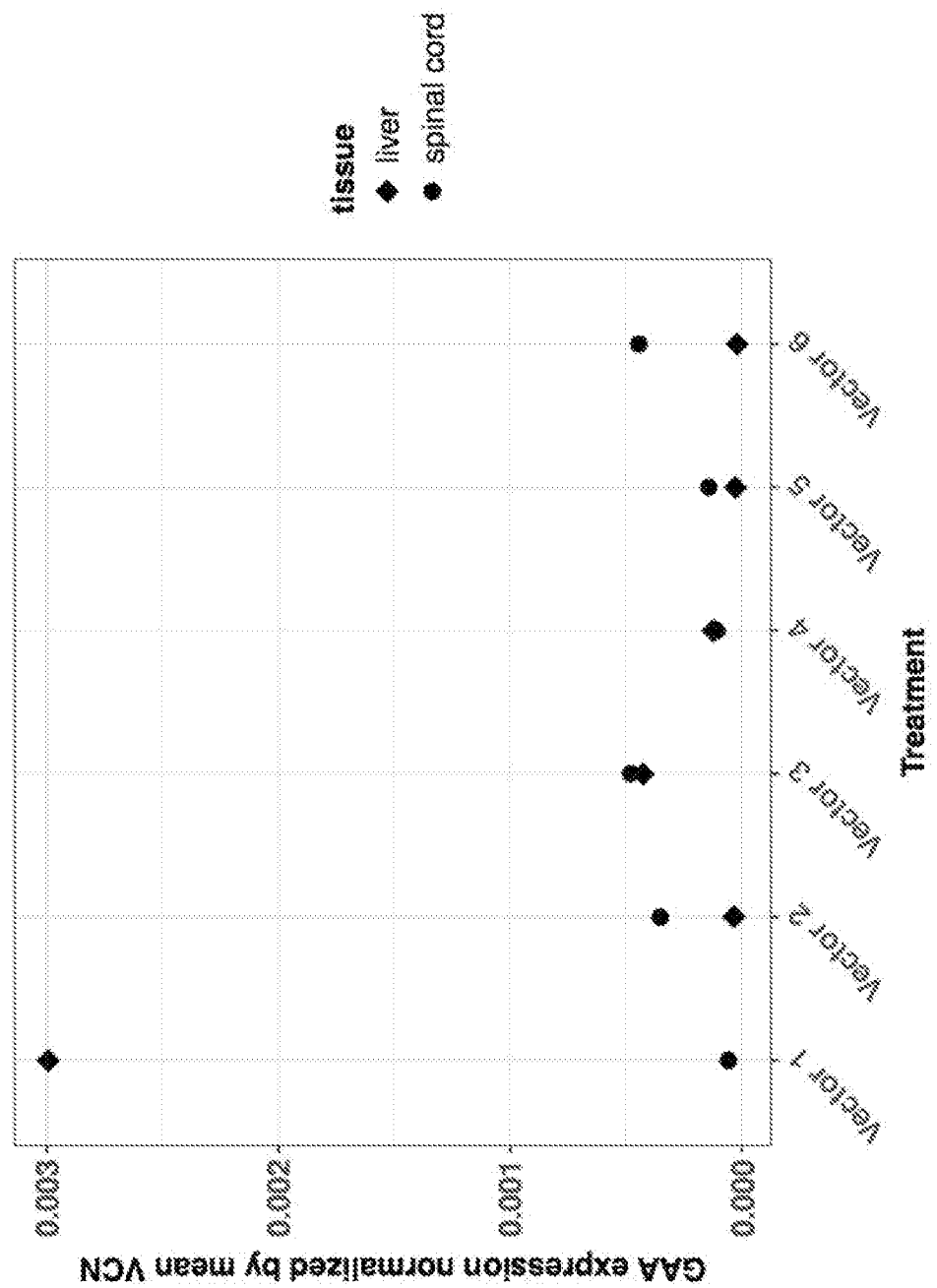
FIG. 11 is a graph showing the levels of RNA expression in liver and spinal cord one month post-dosing, as determined by RNA-Seq analysis, divided by the mean vector copy number (VCN) in liver or brain tissue to estimate a ratio of per-vector expression levels in liver or CNS tissue, respectively.

1  Normal
2  Large and small glycogen aggregates seen in 10-49% of fibers
3  Large and small glycogen aggregates seen in 50-90% of fibers
4  Small glycogen aggregates in >90% of fibers, with large glycogen aggregates only in rare fibers
5  Small glycogen aggregates in >90% of fibers, with large glycogen aggregates in >30% of fibers Evidence for GAA Activity and De Novo GAA Transcripts Associated with Vector 3 in Spinal Cord To assess the ability of hybrid vectors to repair CNS-based Pompe manifestations, GAA activity was assessed one month post-dosing in spinal cord from male (black dots) and female mice (grey triangles) for control- and vector-treated mice dosed at $3\times10^{13}$ vg/kg (FIG. 9). Additionally, hGAA transcripts were measured in spinal cord tissue from male (dots) and female mice (triangles) for control- and vector-treated mice dosed at $1\times10^{13}$ vg/kg by RNA-seq analysis (FIG. 10). Median expression levels of endogenous murine GAA are indicated by the horizontal lines. The levels of RNA expression in liver and spinal cord, as determined by RNA-Seq analysis, were divided by the mean vector copy number (VCN) in liver or brain tissue to estimate a ratio of per-vector expression levels in liver or CNS tissue, respectively (FIG. 11).

The results show evidence for GAA activity and de novo GAA transcripts from Vector 3 in spinal cord tissue. Expression in spinal cord for Vector 3 was equivalent, on a per-VCN basis, to expression in liver Conclusions As shown by this Example, an engineered, synthetic hybrid promoter, such as that in Vector 3, directed bona fide hGAA expression in muscle, liver, and CNS tissue. The liver contribution led to a favorable immunogenicity profile, e.g., for Vector 3. The muscle contribution also leads to favorable GAA activity, glycogen recovery, and pathology observations in muscle, e.g., for Vector 3. Additionally, there is evidence of CNS activity (e.g., for Vector 3), as based on GAA activity in spinal cord and de novo transcripts. Our findings support the clinical translation of the vectors described herein as optimized hGAA vectors for AAV gene therapy for Pompe disease.

Example 2. Treatment of Pompe Disease by Administration of Vectors Containing a GAA Transgene Pperably Linked to a Transcriptional Control Element Using conventional molecular biology techniques known in the art, a gene encoding a therapeutic protein, such as GAA, can be operably linked to a transcription regulatory element (e.g., a transcription regulatory element described in Example 1, above). The gene can subsequently be incorporated into a vector, such as a viral vector, and administered to a patient suffering from a disease associated with a deficiency in the gene. For instance, a patient suffering from Pompe disease, a lysosomal storage disorder characterized by a deficiency in GAA, can be administered a viral vector containing a GAA gene under the control of a transcriptional regulatory element that promotes GAA expression in muscle cells, neurons, and liver cells. For instance, an AAV vector, such as a pseudotyped AAV2/8 or AAV2/9 vector, can be generated that incorporates the GAA gene between the 5' and 3' inverted terminal repeats of the vector, and the gene may be placed under control of a transcriptional regulatory element described in Example 1, above. The AAV vector can be administered to the subject by a variety of routes of administration, such as intravenously, intramuscularly, or subcutaneously, among others.

Following administration of the vector to a patient, a practitioner of skill in the art can monitor the expression of the GAA gene, and the patient's improvement in response to the therapy, by a variety of methods. For instance, a physician can monitor the patient's muscle function (e.g., cardiac muscle function) and/or glycogen accumulation in order to ascertain the patient's response to the therapy. A finding that the patient's muscle function has improved and/or glycogen accumulation levels have decreased following administration of the therapy may indicate that the patient is responding favorably to the treatment. Subsequent doses can be determined and administered as needed.

Other Embodiments

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the invention that come within known or customary practice within the art to which the invention pertains and may be applied to the essential features hereinbefore set forth, and follows in the scope of the claims.

Other embodiments are within the claims.

The invention claimed is:

1. A nucleic acid regulatory element comprising:
   (i) a first segment;
   (ii) a second segment; and
   (iii) a third segment;
   wherein the components are operably linked to each other in a 5'-to-3' direction as:
   first segment-second segment-third segment;
   and wherein:
   the first segment comprises a synapsin promoter having the nucleic acid sequence of SEQ ID NO: 8,
   the second segment comprises an apolipoprotein E hepatic control region (ApoE-HCR) having the nucleic acid sequence of SEQ ID NO: 1, and
   the third segment comprises a desmin promoter having the nucleic acid sequence of SEQ ID NO: 7.

2. A vector comprising the nucleic acid regulatory element of claim 1, wherein the nucleic acid regulatory element is operably linked to a transgene, and wherein the nucleic acid regulatory element induces expression of the transgene upon introduction of the vector into a cell.

3. The vector of claim 2, wherein:
   (i) the transgene is acid alpha-glucosidase (GAA); and/or
   (ii) the cell is a muscle cell, a neuron, or a hepatocyte.

4. The vector of claim 2, wherein the vector is a viral vector.

5. The vector of claim 4, wherein the viral vector is an adeno-associated virus (AAV).

6. The vector of claim 5, wherein the AAV is an AAV1, AAV2, AAV3, AAV4, AAV5, AAV6, AAV7, AAV8, AAV9, or AAVrh74 serotype.

7. The vector of claim 4, wherein the viral vector is a pseudotyped AAV.

8. The vector of claim 7, wherein the pseudotyped AAV is rAAV2/8 or rAAV2/9.

9. A composition comprising a nucleic acid molecule comprising the nucleic acid regulatory element of claim 1, wherein the composition is a liposome, vesicle, synthetic vesicle, exosome, synthetic exosome, dendrimer, or nanoparticle.

10. A method of expressing a transgene in a cell, the method comprising contacting the cell with the vector of claim 2 for a time sufficient to stimulate transcription of the transgene in the cell.

11. A kit comprising the vector of claim 2, wherein the kit further comprises a package insert instructing a user of the kit to contact the vector or composition with a cell, thereby expressing a transgene operably linked to the regulatory control element.

* * * * *